United States Patent [19]

Mencke et al.

[11] Patent Number: 5,589,503

[45] Date of Patent: Dec. 31, 1996

[54] ENDOPARASITICIDAL COMPOSITIONS

[75] Inventors: Norbert Mencke, Leverkusen; Achim Harder, Köln; Peter Jeschke, Leverkusen, all of Germany

[73] Assignee: Bayer Aktiengesellschaft, Leverkusen, Germany

[21] Appl. No.: 368,515

[22] Filed: Jan. 4, 1995

[30] Foreign Application Priority Data

Jan. 11, 1994 [DE] Germany ............................ 44 00 464.8

[51] Int. Cl.$^6$ ................................................. A61K 31/335
[52] U.S. Cl. ............................................................. 514/450
[58] Field of Search ............................................... 514/450

[56] References Cited

FOREIGN PATENT DOCUMENTS 0634408  1/1995  European Pat. Off. ..... A61K 31/395

OTHER PUBLICATIONS

Biosci. Biotech. Biochem., 58 (6), 1193 (1994).
The Journal of Antibiotics, 47, 1322 (1994) By S. J. Nelson pp. 1322–1327.
WO 9419334–A (Abstract) Feb. 19, 1993.
WO 93/19053 (Abstract) Mar. 8, 1993.
Ooyama et al 1993 121:CA:180229e.
Sasaki et al 119 CA:224429k, 1993.
Isogai et al. 99CA: 48503n 1983.

*Primary Examiner*—Russell Travers
*Attorney, Agent, or Firm*—Sprung Horn Kramer & Woods

[57] ABSTRACT

The present invention relates to the use of praziquantel and epsiprantel for enhancing the endoparasiticidal activity of cyclic depsipeptides in endoparasiticidal compositions.

5 Claims, No Drawings

ENDOPARASITICIDAL COMPOSITIONS

The present invention relates to the use of praziquantel and epsiprantel for enhancing the endoparasiticidal activity of cyclic depsipeptides in endoparasiticidal compositions.

Praziquantel 2-(cyclohexylcarbonyl)-1,2,3,6,7,11b-hexahydro-4H-pyrazino[2,1-a]isoquinolin-4-one and its activity against endoparasites is disclosed in GB Patent 1 441 554.

Epsiprantel 2-(cyclohexylcarbonyl)-2,3,6,7,8,12b-hexahydro-pyrazino[2,1-a][2]-benzazepin -4(1H)-one and its activity against endoparasites is disclosed in EP-OS [European Published Specification] 134 984, EP-OS [European Published Specification] 185 012.

A cyclic depsipeptide PF 1022 and its activity against endoparasites is disclosed in EP-OS [European Published Specification] 382 173.

Other cyclic depsipeptides and their endoparasiticidal activity are the subject of non-prior-published patent applications (German Patent Applications P 4 317 432.9; P 4 317 457.4; P 4 317 458.2).

The present invention relates to the use of praziquantel and epsiprantel for enhancing the endoparasiticidal activity of cyclic depsipeptides composed of amino acids and hydroxycarboxylic acids as ring components and 6 to 30 ring atoms.

The present invention furthermore relates to endoparasiticidal compositions containing praziquantel and epsiprantel together with cyclic depsipeptides composed of amino acids and hydroxycarboxylic acids as ring components and 6 to 30 ring atoms.

The present invention furthermore relates to the use of praziquantel and epsiprantel together with cyclic depsipeptides composed of amino acids and hydroxycarboxylic acids as ring components and 6 to 30 ring atoms for the preparation of endoparasiticidal compositions.

Preferred cyclic depsipeptides are those having 18 to 24 ring atoms.

The depsipeptides having 18 ring atoms include compounds of the general formula (I)

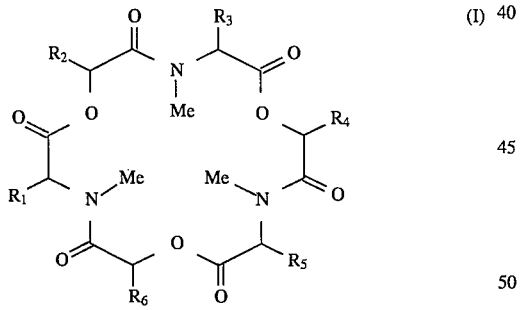

in which

R$^1$, R$^3$ and R$^5$ independently of one another represent hydrogen, straight-chain or branched alkyl having up to 8 carbon atoms, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl which can optionally be substituted by one or two benzyloxycarbonyl radicals or by one, two, three or four alkyl radicals, alkoxycarbonylaminoalkyl, 9-fluorenylmethoxycarbonyl(Fmoc)aminoalkyl, alkenyl, cycloaklyl, cycloalkylalkyl and optionally substituted arylalkyl, substituents which may be mentioned being halogen, hydroxyl, alkyl and alkoxy, R$^2$, R$^4$ and R$^6$ independently of one another represent hydrogen, straight-chain or branched alkyl having up to 8 carbon atoms, hydroxyalkyl, mercaptoalkyl, alkanoyloxyalkyl, alkoxyalkyl, aryloxyalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, alkoxycarbonylaminoalkyl, alkenyl, cycloalkyl, cycloalkylalkyl, optionally substituted aryl or arylalkyl, substituents which may be mentioned being halogen, hydroxyl, alkyl and alkoxy, and their optical isomers and racemates.

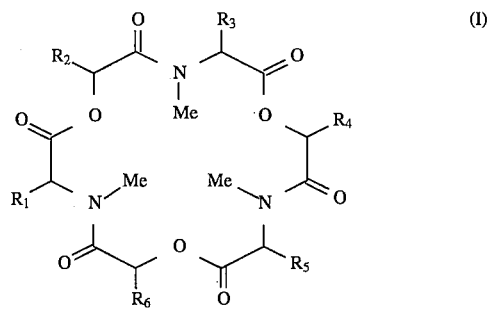

Preferred compounds of the formula (I) are those in which

R$^1$, R$^3$ and R$^5$ independently of one another straight-chain or branched C$_1$–C$_8$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tertheptyl, octyl, isooctyl, sec-octyl, hydroxy-C$_1$–C$_6$-alkyl, in particular hydroxymethyl, 1-hydroxyethyl, C$_1$–C$_4$-alkanoyloxy-C$_1$–C$_6$-alkyl, in particular acetoxymethyl, 1-acetoxyethyl, C$_1$–C$_4$-alkoxy-C$_1$–C$_6$-alkyl, in particular methoxymethyl, 1-methoxyethyl, aryl-C$_1$–C$_4$-alkyloxy-C$_1$–C$_6$-alkyl, in particular benzyloxymethyl, 1-benzyloxy-ethyl, mercapto-C$_1$–C$_6$-alkyl, in particular mercaptomethyl, C$_1$–C$_4$-alkylthio-C$_1$–C$_6$-alkyl, in particular methylthioethyl, C$_1$–C$_4$-alkylsulphinyl-C$_1$–C$_6$-alkyl, in particular methylsulphinylethyl, C$_1$–C$_4$-alkylsulphonyl-C$_1$–C$_6$-alkyl, in particular methylsulphonylethyl, carboxy-C$_1$–C$_6$-alkyl, in particular carboxymethyl, carboxyethyl, C$_1$–C$_4$-alkoxycarbonyl-C$_1$–C$_6$-alkyl, in particular methoxycarbonylmethyl, ethoxycarbonylethyl, C$_1$–C$_4$-arylalkoxycarbonyl-C$_1$–C$_6$-alkyl, in particular benzyloxycarbonylmethyl, carbamoyl-C$_1$–C$_6$-alkyl, in particular carbamoylmethyl, carbamoylethyl, amino-C$_1$–C$_6$-alkyl, in particular aminopropyl, aminobutyl, C$_1$–C$_4$-alkylamino-C$_1$–C$_6$-alkyl, in particular methylaminopropyl, methylaminobutyl, C$_1$–C$_4$-dialkylamino, C$_1$–C$_6$-alkyl, in particular dimethylaminopropyl, dimethylaminobutyl, guanido-C$_1$–C$_6$-alkyl, in particular guanidopropyl, C$_1$–C$_4$-alkoxycarbonylamido-C$_1$–C$_6$-alkyl, in particular tert-butoxycarbonylaminopropyl, tert-butoxycarbonylaminobutyl, 9-fluorenylmethoxycarbonyl(Fmoc)amino-C$_1$–C$_6$-alkyl, in particular 9-fluorenylmethoxycarbonyl(Fmoc)aminopropyl, 9-fluorenylmethoxycarbonyl(Fmoc)aminobutyl, C$_2$–C$_8$-alkenyl, in particular vinyl, allyl, butenyl, C$_3$–C$_7$-cycloalkyl, in particular cyclopentyl, cyclohexyl, cycloheptyl, C$_3$–C$_7$-cycloalkyl-C$_1$–C$_4$-alkyl, in particular cyclopentylmethyl, cyclohexylmethyl, cycloheptylmethyl, phenyl-C$_1$–C$_4$-alkyl, in particular phenylmethyl which can optionally be substituted by radicals from the series comprising halogen, in particular fluorine, chlorine bromine or iodine, hydroxyl, $C_1$–$C_4$-alkoxy, in particular methoxy or ethoxy, or $C_1$–$C_4$-alkyl, in particular methyl, $R^2$, $R^4$ and $R^6$ independently of one another straight-chain or branched $C_1$–$C_8$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxy-$C_1$–$C_6$-alkyl, in particular hydroxymethyl, 1-hydroxyethyl, $C_1$–$C_4$-alkanoyloxy-$C_1$–$C_6$-alkyl, in particular acetoxymethyl, 1-acetoxyethyl, $C_1$–$C_4$-alkoxy-$C_1$–$C_6$-alkyl, in particular methoxymethyl, 1-methoxyethyl, aryl-$C_1$–$C_4$-alkyloxy-$C_1$–$C_6$-alkyl, in particular benzyloxymethyl, 1-benzyloxy-ethyl, mercapto-$C_1$–$C_6$-alkyl, in particular mercaptomethyl, $C_1$–$C_4$-alkylthio-$C_1$–$C_6$-alkyl, in particular methylthioethyl, $C_1$–$C_4$-alkylsulphinyl-$C_1$–$C_6$-alkyl, in particular methylsulphinylethyl, $C_1$–$C_4$-alkylsulphonyl-$C_1$–$C_6$-alkyl, in particular methylsulphonylethyl, carboxy-$C_1$–$C_6$-alkyl, in particular carboxymethyl, carboxyethyl, $C_1$–$C_4$-alkoxycarbonyl-$C_1$–$C_6$-alkyl, in particular methoxycarbonylmethyl, ethoxycarbonylethyl, $C_1$–$C_4$-arylalkoxycarbonyl-$C_1$–$C_6$-alkyl, in particular benzyloxycarbonylmethyl, carbamoyl-$C_1$–$C_6$-alkyl, in particular carbamoylmethyl, carbamoylethyl, amino-$C_1$–$C_6$-alkyl, in particular aminopropyl, aminobutyl, $C_1$–$C_4$-alkylamino-$C_1$–$C_6$-alkyl, in particular methylaminopropyl, methylaminobutyl, $C_1$–$C_4$-dialkylamino-$C_1$–$C_6$-alkyl, in particular dimethylaminopropyl, dimethylaminobutyl, $C_2$–$C_8$-alkenyl, in particular vinyl, allyl, butenyl, $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, phenyl, phenyl-$C_1$–$C_4$-alkyl, in particular phenylmethyl which can optionally be substituted by radicals from the series comprising halogen, in particular fluorine, chlorine bromine or iodine, hydroxyl, $C_1$–$C_4$-alkoxy, in particular methoxy or ethoxy, or $C_1$–$C_4$-alkyl, in particular methyl, and their optical isomers and racemates.

Particularly preferred compounds of the formula (I) are those
in which $R^1$, $R^3$ and $R^5$ independently of one another straight-chain or branched $C_1$–$C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, hydroxy-$C_1$–$C_6$-alkyl, in particular hydroxymethyl, 1-hydroxyethyl, $C_1$–$C_4$-alkanoyloxy-$C_1$–$C_6$-alkyl, in particular acetoxymethyl, 1-acetoxyethyl, $C_1$–$C_4$-alkoxy-$C_1$–$C_6$-alkyl, in particular methoxymethyl, 1-methoxyethyl, aryl-$C_1$–$C_4$-alkyloxy-$C_1$–$C_6$-alkyl, in particular benzyloxymethyl, 1-benzyloxyethyl, $C_1$–$C_4$-alkoxycarbonylamino-$C_1$–$C_6$-alkyl, in particular tert-butoxycarbonylaminopropyl, tert-butoxycarbonylaminobutyl, $C_2$–$C_8$-alkenyl, in particular vinyl, allyl, $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, phenyl-$C_1$–$C_4$-alkyl, in particular phenylmethyl, which can optionally be substituted by one or more identical or different radicals from amongst those mentioned above, $R^2$, $R^4$ and $R^6$ independently of one another straight-chain or branched $C_1$–$C_8$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxy-$C_1$–$C_6$-alkyl, in particular hydroxymethyl, aryl-$C_1$–$C_4$-alkyloxy-$C_1$–$C_6$-alkyl, in particular benzyloxymethyl, 1-benzyloxyethyl, carboxy-$C_1$–$C_6$-alkyl, in particular carboxymethyl, carboxyethyl, $C_1$–$C_4$-alkoxycarbonyl-$C_1$–$C_6$-alkyl, in particular methoxycarbonylmethyl, ethoxycarbonylethyl, $C_1$–$C_4$-arylalkoxycarbonyl-$C_1$–$C_6$-alkyl, in particular benzyloxycarbonylmethyl, $C_1$–$C_4$-alkylamino-$C_1$–$C_6$-alkyl, in particular methylaminopropyl, methylaminobutyl, $C_1$–$C_4$-dialkylamino-$C_1$–$C_6$-alkyl, in particular dimethylaminopropyl, dimethylaminobutyl, $C_2$–$C_8$-alkenyl, in particular vinyl, allyl, butenyl, $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptyl-methyl, phenyl, phenyl-$C_1$–$C_4$-alkyl, in particular phenylmethyl which can optionally be substituted by one or more identical or different radicals from amongst those mentioned above, and their optical isomers and racemates.

Very particularly preferred compounds of the formula (I) are those
in which $R^1$, $R^3$ and $R^5$ independently of one another straight-chain or branched $C_1$–$C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl $C_2$–$C_8$-alkenyl, in particular allyl, $C_3$–$C_7$-cycloalkyl-$C_1$–$C_4$-alkyl, in particular cyclohexylmethyl, phenyl-$C_1$–$C_4$-alkyl, in particular phenylmethyl, $R^2$, $R^4$ and $R^6$ independently of one another straight-chain or branched $C_1$–$C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, $C_2$–$C_8$-alkenyl, in particular vinyl, allyl, $C_3$–$C_7$-cycloalkyl-$C_1$–$C_4$-alkyl, in particular cyclohexylmethyl, phenyl-$C_1$–$C_4$-alkyl, in particular phenylmethyl which can optionally be substituted by one or more identical or different radicals from amongst those mentioned above, and their optical isomers and racemates.

All compounds of the general formula (I) which can exist in optically active, stereoisomeric forms or in the form of racemic mixtures can be used in the sense of the present invention. However, the optically active, stereoisomeric forms of the compounds of the general formula (I) are preferably used according to the invention.

The following compounds of the general formula (I) in which the radicals $R^1$ to $R^6$ have the meaning given below may be mentioned individually:

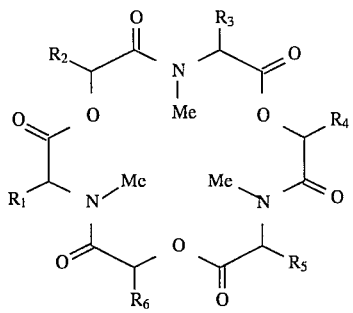

| R¹ | R² | R³ | R⁴ | R⁵ | R⁶ |
|---|---|---|---|---|---|
| —CHMeCH₂Me | -Cyclohexyl | —CHMeCH₂Me | —Me | —CHMeCH₂Me | —Me |
| —CHMeCH₂Me | -Cyclohexyl | —CHMeCH₂Me | —Me | —CHMeCH₂Me | -Cyclohexyl |
| —CHMeCH₂Me | —CH₂—Phe | —CHMeCH₂Me | —Me | —CHMeCH₂Me | —Me |
| —CHMeCH₂Me | —CH₂—Phe | —CHMeCH₂Me | —Me | —CHMeCH₂Me | —CH₂—Phe |
| —CHMeCH₂Me | —(CH₂)₃—Me | —CHMeCH₂Me | —Me | —CHMeCH₂Me | —Me |
| —CHMeCH₂Me | —(CH₂)₃—Me | —CHMeCH₂Me | —Me | —CHMeCH₂Me | —(CH₂)₃—Me |
| —CHMe₂ | —CH₂—Phe | —CHMeCH₂Me | —Me | —CHMeCH₂Me | —Me |
| —CH₂—Phe | —CHMe₂ | —CH₂—Phe | —CHMe₂ | —CHMeCH₂Me | —CHMe₂ |
| —CH₂CHMe₂ | —CH₂—Phe | —CH₂CHMe₂ | —Me | —CH₂CHMe₂ | —CH₂—Phe |
| —(CH₂)₃—Me | —Me | —CHMeCH₂Me | —Me | —CHMeCH₂Me | —Me |
| —CHMe₂ | —Me | —CHMe₂ | —Me | —CHMe₂ | —Me |
| —CH₂—Me | —Me | —CH₂—Me | —Me | —CH₂—Me | —Me |
| —(CH₂)₃—Me | —Me | —(CH₂)₃—Me | —Me | —(CH₂)₃—Me | —Me |
| —(CH₂)₃—Me | —Me | —(CH₂)₃—Me | —Me | —(CH₂)₃—Me | —Me |
| —CH₂—CH=CH₃ | —Me | —CH₂—CH=CH₃ | —Me | —(CH₂)—CH=CH₂ | —Me |
| —CHMeCH₂Me | —Me | —CHMeCH₂Me | —Me | —CHMeCH₂Me | —CH₂—Me |
| —CHMeCH₂Me | —Me | —CHMeCH₂Me | —Me | —CHMeCH₂Me | —(CH₂)₃—Me |
| —CHMeCH₂Me | —Me | —CHMeCH₂Me | —Me | —CHMeCH₂Me | —(CH₂)₃—Me |
| —CHMeCH₂Me | —Me | —CHMeCH₂Me | —Me | —CH₂Me | —Me |
| —CHMeCH₂Me | —Me | —CHMeCH₂Me | —Me | —(CH₂)₃—Me | —Me |
| -Cyclohexyl | —Me | -Cyclohexyl | —Me | -Cyclohexyl | —Me |
| —CH₂CHMe₂ | -Cyclohexyl | —CH₂CHMe₂ | —Me | —CH₂CHMe₂ | -Cyclohexyl |
| —CH₂CHMe₂ | -Cyclohexyl | —CH₂CHMe₂ | —Me | —CH₂CHMe₂ | —Me |
| —CHMeCH₂Me | —CHMe₂ | —CHMeCH₂Me | —CHMe₂ | —CHMeCH₂Me | —Me |
| —CH₂—Phe | —Me | —CH₂—Phe | —Me | —CH₂—Phe | —Me |
| -Cyclohexyl | —Me | -Cyclohexyl | —Me | -Cyclohexyl | —Me |
| —CHMe₂ | —CHMe₂ | —CHMe | —Me | —CHMe₂ | —Me |
| —CHMe₂ | —CHMe₂ | —CHMe₂ | —CHMe₂ | —CHMe₂ | —Me |
| —CH₂—Me | —CHMe₂ | —CH₂Me | —Me | —CH₂—Me | —Me |
| —CH₂—Me | —CHMe₂ | —CHMe₂ | —CHMe₂ | —CH₂—Me | —Me |
| —(CH₂)₃—Me | —CHMe₂ | —(CH₂)₃—Me | —Me | —(CH₂)₃—Me | —Me |
| —(CH₂)₃—Me | —CHMe₂ | —(CH₂)₃—Me | —CHMe₂ | —(CH₂)₃—Me | —Me |
| —(CH₂)₃—Me | —CHMe₂ | —(CH₂)₃—Me | —Me | —(CH₂)₃—Me | —Me |
| —(CH₂)₃—Me | —CHMe₂ | —(CH₂)₃—Me | —CHMe₂ | —(CH₂)₃—Me | —Me |
| —CH₂—CH=CH₂ | —CHMe₂ | —CH₂—CH=CH₂ | —Me | —CH₂—CH=CH₂ | —Me |
| —CH₂—CH=CH₂ | —CHMe₂ | —CH₂—CH=CH₂ | —CHMe₂ | —CH₂—CH=CH₂ | —Me |
| —Me | —Me | —CHMeCH₂Me | —Me | —CH₂—Me | —Me |
| —Me | —Me | —CHMeCH₂Me | —Me | —(CH₂)₃—Me | —Me |

Me = methyl; Phe = phenyl

Another depsipeptide which may be mentioned is the compound PF 1022, which is disclosed in EP-OS [European Published Specification] 382 173 and has the following formula

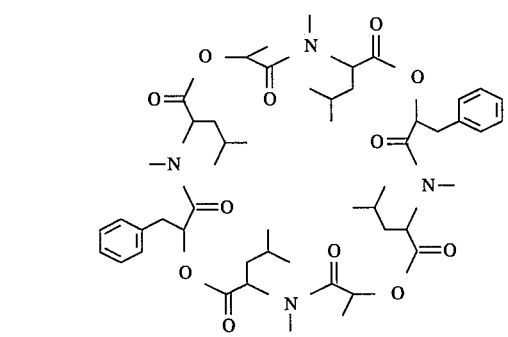

Other depsipeptides which may be mentioned are the compounds disclosed in PCT Application WO 93/19053.

Compounds of PCT Application WO 93/19053 which may be mentioned in particular are those of the following formula:

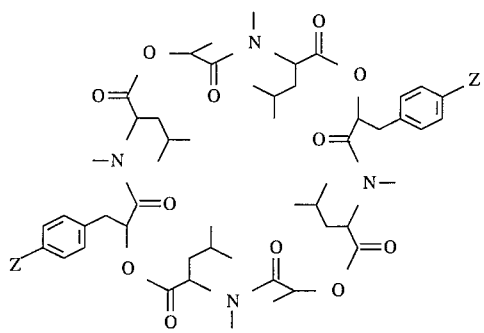

in which

Z represents N-morpholinyl, nitro, amino, mono- or dimethylamino.

Compounds which may additionally be mentioned are those of the following formula:

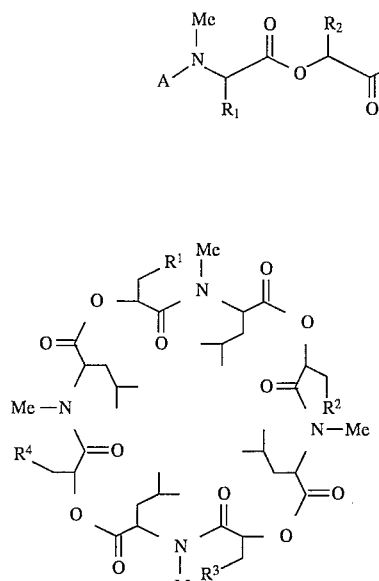

in which $R^1$, $R^2$, $R^3$ and $R^4$ independently of one another represent hydrogen, $C_1$–$C_{10}$-alkyl or aryl, in particular phenyl, each of which is optionally substituted by hydroxyl, $C_1$–$C_{10}$-alkoxy or halogen.

Some of the compounds of the general formula (I) are known (by isolation, cf. for example: R. Zocher et al., J. Antibiotics 45 (1992) pp. 1273–1277 [enniatins A, B and C]; Hiroshi Tomoda et al. J. Antibiotics 45 (1992) pp. 1207–1215 [enniatins A, A₁, B, B₁, D, E and F]; by synthesis, cf. for example: P. Quitt et al., Helv. Chimica Acta 46 (1963) pp. 1715–1720; P. Quitt et al., Chimica Acta 46 (1963) pp. 1715–1720; P. Quitt et al., Helv. Chimica Acta 47 (1964) pp. 166–173 [enniatin A]; Pl. A. Plattner et al., Helv. Chimica Acta 46 (1963) pp. 927–935 [enniatin B]; Yu. A. Ovchinnikov et al. Tetrahedron Lett. 2 (1971) pp. 159–162; R. W. Roeske et al. Biochem. Biophys. Res. Commun. 57 (1974) pp. 554–561 [beauvericin]; Yu. A. Ovchinnikov et al. Zh. Obshch. Khim. 42 (10) (1972) pp. 2320–2334; ref. C. A. 78, 58 77 k) or can be obtained by the processes described therein.

The compounds of the formula (I) can be synthesized by the process applied by U. Schmidt et al. to macrocyclic peptide alkaloids (cf. for example: U. Schmidt et al. in Synthesis (1991) pp. 294–300 [didemnin A, B and C]; Angew. Chem. 96 (1984) pp. 723–724 [dolastatin 3]; Angew. Chem. 102 (1990) pp. 562–563 [fenestin A]; Angew. Chem. 97 (1985) pp. 606–607 [ulicyclamid]; J. Org. Chem. 47 (1982) pp. 3261–3264).

Compounds of the formula (I) are prepared by a) subjecting carboxyl-activated open-chain hexadepsipeptides of the general formula (II-a)

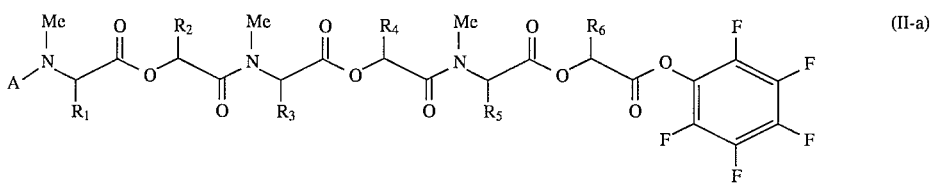

in which

A represents an amino protective group which can be eliminated selectively with regard to the active ester protective group, such as benzyl or benzyl-oxycarbonyl, and $R^1$, $R^2$, $R^3$, $R^4$, $R^5$ and $R^6$ have the above-mentioned meaning, to a cyclization reaction in the presence of a hydrogenation catalyst, in the presence of a basic reaction auxiliary and in the presence of a diluent, or b) subjecting open-chain hexadepsipeptides of the general formula (II-b)

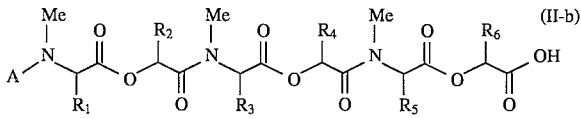

in which $R^1$, $R^2$, $R^3$, $R^4$, $R^5$ and $R^6$ have the above-mentioned meaning, to a cyclization reaction in the presence of a coupling reagent, in the presence of a basic reaction auxiliary and in the presence of a diluent.

If, in process a) for the preparation of the new cyclic hexadepsipeptides (enniatins) (I), pentafluorophenyl N-benzyloxycarbonyl-N-methyl-L-isoleucyl-D-lactyl-N-methyl-L-isoleucyl-D-lactyl-N-methyl-L-isoleucyl-D-lactate is employed as compounds of the formula (II), the process can be represented by the following equation:

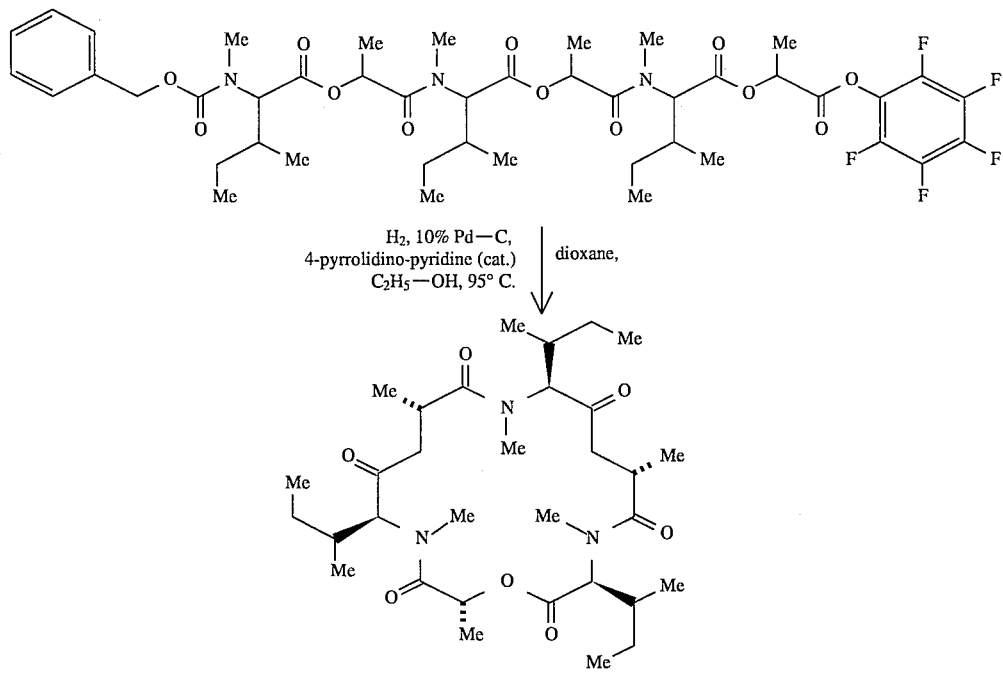

Formula (II) provides a general definition of the carboxyl-activated derivaves of the open-chain hexadepsipeptides required as starting substances for carrying out process a. In this formula, A and $R^1$ to $R^6$ preferably represent those radicals which have already been mentioned in connection with the description of the substances of the formula (I) according to the invention as being preferred for these substituents.

The carboxyl-activated pentafluorophenyl esters of the formula (II-a) which are used as starting materials can be obtained by processes known from the literature (cf. L. Kisfaludy et al. J. Org. Chem. 35 (1970), p. 3563; L. Kisfaludy et al. J. Org. Chem. 44 (1979), pp. 654–655). Their preparation is described further below.

The following compounds of the general formula (IIa) in which the radicals A and $R^1$ to $R^6$ have the meaning given below may be mentioned individually:

| A  | $R^1$           | $R^2$           | $R^3$           | $R^4$    | $R^5$           | $R^6$           |
|----|-----------------|-----------------|-----------------|----------|-----------------|-----------------|
| Z  | —CHMeCH$_2$Me   | -Cyclohexyl     | —CHMeCH$_2$Me   | —Me      | —CHMeCH$_2$Me   | —Me             |
| Bn | —CHMeCH$_2$Me   | -Cyclohexyl     | —CHMeCH$_2$Me   | —Me      | —CHMeCH$_2$Me   | -Cyclohexyl     |
| Bn | —CHMeCH$_2$Me   | —CH$_2$—Phe     | —CHMeCH$_2$Me   | —Me      | —CHMeCH$_2$Me   | —Me             |
| Bn | —CHMeCH$_2$Me   | —CH$_2$—Phe     | —CHMeCH$_2$Me   | —Me      | —CHMeCH$_2$Me   | —CH$_2$—Phe     |
| Z  | —CHMeCH$_2$Me   | —(CH$_2$)$_3$—Me| —CHMeCH$_2$Me   | —Me      | —CHMeCH$_2$Me   | —Me             |
| Z  | —CHMeCH$_2$Me   | —(CH$_2$)$_3$—Me| —CHMeCH$_2$Me   | —Me      | —CHMeCH$_2$Me   | —Me             |
| Bn | —CHMeCH$_2$Me   | —(CH$_2$)$_3$—Me| —CHMeCH$_2$Me   | —Me      | —CHMeCH$_2$Me   | —(CH$_2$)$_3$—Me|
| Bn | —CHMe$_2$       | —CH$_2$—Phe     | —CHMeCH$_2$Me   | —Me      | —CHMeCH$_2$Me   | —Me             |
| Z  | —CH$_2$—Phe     | —CHMe$_2$       | —CH$_2$—Phe     | —CHMe$_2$| —CHMeCH$_2$Me   | —CHMe$_2$       |
| Bn | —CH$_2$CHMe$_2$ | —CH$_2$—Phe     | —CH$_2$CHMe$_2$ | —Me      | —CH$_2$CHMe$_2$ | —CH$_2$—Phe     |
| Bn | —CH$_2$—Me      | —Me             | —CH$_2$—Me      | —Me      | —CH$_2$—Me      | —Me             |
| Z  | —(CH$_2$)$_3$—Me| —Me             | —(CH$_2$)$_3$—Me| —Me      | —(CH$_2$)$_3$—Me| —Me             |
| Bn | —(CH$_2$)$_3$—Me| —Me             | —(CH$_2$)$_3$—Me| —Me      | —(CH$_2$)$_3$—Me| —Me             |
| Bn | —CH$_2$—CH=CH$_2$| —Me            | —CH$_2$—CH=CH$_2$| —Me     | —CH$_2$—CH=CH$_2$| —Me            |
| Z  | —CHMeCH$_2$Me   | —Me             | —CHMeCH$_2$Me   | —Me      | —CHMeCH$_2$Me   | —CH$_2$—Me      |
| Z  | —CHMeCH$_2$Me   | —Me             | —CHMeCH$_2$Me   | —Me      | —CHMeCH$_2$Me   | —(CH$_2$)$_3$—Me|
| Z  | —CHMeCH$_2$Me   | —Me             | —CHMeCH$_2$Me   | —Me      | —CHMeCH$_2$Me   | —(CH$_2$)$_3$—Me|
| Z  | —CHMeCH$_2$Me   | —Me             | —CHMeCH$_2$Me   | —Me      | —CH$_2$Me       | —Me             |
| Z  | —CHMeCH$_2$Me   | —Me             | —CHMeCH$_2$Me   | —Me      | —(CH$_2$)$_3$—Me| —Me             |
| Bn | -Cyclohexyl     | —Me             | -Cyclohexyl     | —Me      | -Cyclohexyl     | —Me             |

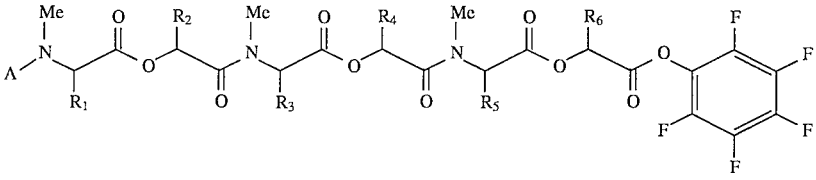

| A | R¹ | R² | R³ | R⁴ | R⁵ | R⁶ |
|---|---|---|---|---|---|---|
| Z | —CH$_2$CHMe$_2$ | -Cyclohexyl | —CH$_2$CHMe$_2$ | —Me | —CH$_2$CHMe$_2$ | -Cyclohexyl |
| Z | —CH$_2$CHMe$_2$ | -Cyclohexyl | —CH$_2$CHMe$_2$ | —Me | —CH$_2$CHMe$_2$ | —Me |
| Z | —CHMeCH$_2$Me | —CHMe$_2$ | —CHMeCH$_2$Me | —CHMe$_2$ | —CHMeCH$_2$Me | —Me |
| Bn | —CH$_2$—Phe | —Me | —CH$_2$—Phe | —Me | —CH$_2$—Phe | —Me |
| Bn | -Cyclohexyl | —Me | -Cyclohexyl | —Me | -Cyclohexyl | —Me |
| Z | —CHMe$_2$ | —CHMe$_2$ | —CHMe$_2$ | —Me | —CHMe$_2$ | —Me |
| Z | —CHMe$_2$ | —CHMe$_2$ | —CHMe$_2$ | —CHMe$_2$ | —CHMe$_2$ | —Me |
| Bn | —CH$_2$—Me | —CHMe$_2$ | —CH$_2$—Me | —Me | —CH$_2$—Me | —Me |
| Bn | —CH$_2$—Me | —CHMe$_2$ | —CH$_2$—Me | —CHMe$_2$ | —CH$_2$—Me | —Me |
| Bn | —(CH$_2$)$_3$—Me | —CHMe$_2$ | —(CH$_2$)$_3$—Me | —Me | —(CH$_2$)$_3$—Me | —Me |
| Bn | —(CH$_2$)$_3$—Me | —CHMe$_2$ | —(CH$_2$)$_3$—Me | —CHMe$_2$ | —(CH$_2$)$_3$—Me | —Me |
| Bn | —(CH$_2$)$_3$—Me | —CHMe$_2$ | —(CH$_2$)$_3$—Me | —Me | —(CH$_2$)$_3$—Me | —Me |
| Bn | —(CH$_2$)$_3$—Me | —CHMe$_2$ | —(CH$_2$)$_3$—Me | —CHMe$_2$ | —(CH$_2$)$_3$—Me | —Me |
| Bn | —CH$_2$—CH=CH$_2$ | —CHMe$_2$ | —CH$_2$—CH=CH$_2$ | —Me | —CH$_2$—CH=CH$_2$ | —Me |
| Bn | —CH$_2$—CH=CH$_2$ | —CHMe$_2$ | —CH$_2$—CH=CH$_2$ | —CHMe$_2$ | —CH$_2$—CH=CH$_2$ | —Me |

Bn: —CH$_2$-phenyl; Z: —CO—O—CH$_2$-phenyl; Me = methyl; Phe = phenyl.

The cyclization reaction of the compounds of the formula (II) is preferably carried out in the presence of a suitable hydrogenation catalyst and in the presence of a basic reaction auxiliary using diluents.

Catalysts which are suitable for carrying out process a are all customary hydrogenation catalysts. Noble-metal catalysts, such as, for example, platinum, platinum oxide, palladium or ruthenium, if appropriate on a suitable support, such as, for example, carbon or silicon dioxide, are preferably used.

Basic reaction auxilaries which can be employed are all suitable acid-binding agents, such as amines, in particular tertiary amines, and alkali metal compounds and alkaline earth metal compounds.

Examples which may be mentioned are the hydroxides, oxides and carbonates of lithium, sodium, potassium, magnesium, calcium and barium, furthermore other basic compounds, such as triethylamine, trimethylamine, tribenzylamine, triisopropylamine, tributylamine, tribenzylamine, tricyclohexylamine, triamylamine, trihexylamine, N,N-dimethyl-aniline, N,N-dimethyl-toluidine, N,N-dimethyl-p-aminopyridine, N-methyl-pyrrolidine, N-methyl-piperidine, N-methyl-imidazole, N-methyl-pyrrole, N-methyl-morpholine, N-methyl-hexamethyleneimine, pyridine, 4-pyrrolidino-pyridine, 4-dimethylamino-pyridine, quinoline, α-picoline, β-picoline, isoquinoline, pyrimidine, acridine, N,N,N'-N'-tetramethylene-diamine, N,N,N',N'-tetraethylenediamine, quinoxaline, N-propyl-diisopropylamine, N-ethyl-diisopropylamine, N,N'-dimethylcycl-hexylamine, 2,6-lutidine, 2,4-lutidine, triethylenediamine, diazabicyclooctane (DABCO), diazabicyclononene (DBN) or diazabicycloundecene (DBU).

Heteroaromatic substances, such as, for example, pyridine, N-methyl-imidazole or 4-pyrrolidino-pyridine, are preferably used.

Suitable diluents for carrying out process a are all inert organic solvents.

Examples which may be mentioned are: halogen hydrocarbons, in particular chlorohydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, dichlorobenzene, chlorotoluene, trichlorobenzene; alcohols, such as methanol, ethanol, isopropanol and butanol; ethers, such as ethyl propyl ether, methyl tert-butyl ether, n-butyl ether, di-n-butyl ether, diisobutyl ether, diisoamyl ether, diisopropyl ether, anisole, phenetol, cyclohexyl methyl ether, diethyl ether, ethylene glycol dimethyl ether, tetrahydrofuran, dioxane and dichlorodiethyl ether; nitro hydrocarbons, such as nitromethane, nitroethane, nitrobenzene, chloronitrobenzene and o-nitrotoluene; nitriles, such as acetonitrile, butyronitrile, isobutyronitrile, benzonitrile and m-chlorobenzonitrile; aliphatic, cycloaliphatic or aromatic hydrocarbons, such as heptane, hexane, nonane, cymene, benzine fractions within a boiling point range of 70° C. to 190° C., cyclohexane, methylcyclohexane, petroleum ether, ligroin, octane, benzene, toluene and xylene; esters, such as ethyl acetate and isobutyl acetate; amides, for example formamide, N-methylformamide, N,N-dimethylformamide and N-methylpyrrolidone; ketones, such as acetone and methyl ethyl ketone. Mixtures of the above-mentioned solvents and diluents are also suitable.

Preferred substances are ethers, such as, for example, dioxane, and mixtures of alcohols and ether.

Process a is carried out by heating compounds of the formula (IIa) in a diluent under high-dilution conditions in the presence of hydrogen and in the presence of a basic reaction auxiliary and of a suitable hydrogenation catalyst.

The reaction time is approximately 4 to 20 hours. The reaction is carried out at temperatures between +20° C. and +200° C., preferably between +70° C. and +155° C. The process is preferably carried out under an inert gas atmosphere and under the pressure which is established under the reaction conditions when the mixture is heated to the reaction temperature required.

For carrying out process a according to the invention, a solution of pentafluorophenyl N-benzyloxycarbonyl-N-methyl-L-isoleucyl-D--lactyl-N-methyl-L-isoleucyl-D-lactyl-N-methyl-L-isoleucyl-D-lactate of the formula (IIa) in dioxane is added dropwise in the course of 2 to 10 hours to a rapidly stirred suspension of equimolar amounts of a suitable hydrogenation catalyst, for example palladium/charcoal, in an excess of dioxane at 95° C. while continuously passing through hydrogen. As catalysts, the solution generally contains 0.5 to 2.5 mol, preferably 1.0 to 2.0 mol, of 4-pyrrolidino-pyridine and 0.5 to 10%, preferably 2 to 5%, of alcohol (based on the solvent).

Besides N-benzyloxycarbonyl-substituted pentafluorophenyl esters of the formula (IIa), N-benzyl- and N-tert-butoxycarbonyl-substituted pentafluorophenyl esters of the formula (IIa) can also be used, and the latter substances can be cyclized in a two-phase system as described by U. Schmidt (cf. for example: U. Schmidt et al., Synthesis (1991) pp. 294–300 [didemnin A, B and C]).

When the reaction is complete, the reaction mixture is cooled, the entire reaction batch is concentrated in vacuo and extracted using an organic solvent, and the extract is worked up in a manner known per se. The products obtained can be purified in the customary manner by recrystallization, distillation in vacuo or column chromatography.

If, in process b for the preparation of the new cyclic hexadepsipeptides (enniatins), N-methyl-L-isoleucyl-D-lactyl-N-methyl-L-isoleucyl-D-lactyl-N-methyl-L-isoleucyl-D-lactic acid is employed as compounds of the formula (IIb), the process can be represented by the following equation:

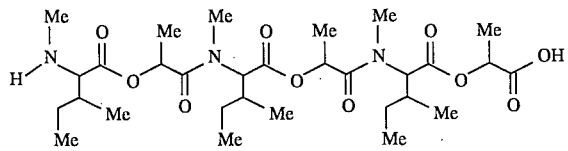

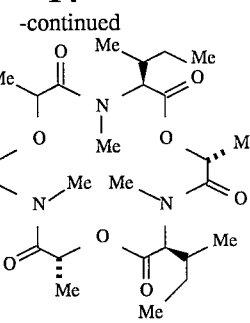

Formula (II) provides a general definition of the open-chain hexadepsipeptides required as starting substances for carrying out process b. In this formula, $R^1$ to $R^6$ preferably represent those radicals which have already been mentioned in connection with the description of the substances of the formula (I) according to the invention as being preferred for these substituents.

The hexadepsipeptides of the formula (II) which are used as starting materials can be obtained by the processes described further below.

The following compounds of the general formula (IIb) in which the radicals $R^1$ to $R^6$ have the meaning given below may be mentioned individually:

(IIb)

| $R^1$ | $R^2$ | $R^3$ | $R^4$ | $R^5$ | $R^6$ |
|---|---|---|---|---|---|
| —CHMeCH2Me | -Cyclohexyl | —CHMeCH$_2$Me | —Me | —CHMeCH$_2$Me | —Me |
| —CHMeCH$_2$Me | -Cyclohexyl | —CHMeCH$_2$Me | —Me | —CHMeCH$_2$Me | -Cyclohexyl |
| —CHMeCH$_2$Me | —CH$_2$—Phe | —CHMeCH$_2$Me | —Me | —CHMeCH$_2$Me | —Me |
| —CHMeCH$_2$Me | —CH$_2$—Phe | —CHMeCH$_2$Me | —Me | —CHMeCH$_2$Me | —CH$_2$—Phe |
| —CHMeCH$_2$Me | —(CH$_2$)$_3$—Me | —CHMeCH$_2$Me | —Me | —CHMeCH$_2$Me | —Me |
| —CHMeCH$_2$Me | —(CH$_2$)$_3$—Me | —CHMeCH$_2$Me | —Me | —CHMeCH$_2$Me | —(CH$_2$)$_3$—Me |
| —CHMe$_2$ | —CH$_2$—Phe | —CHMeCH$_2$Me | —Me | —CHMeCH$_2$Me | —Me |
| —CH$_2$—Phe | —CHMe$_2$ | —CH$_2$—Phe | —CHMe$_2$ | —CHMeCH$_2$Me | —CHMe$_2$ |
| —CH$_2$CHMe$_2$ | —CH$_2$—Phe | —CH$_2$CHMe$_2$ | —Me | —CH$_2$CHMe$_2$ | —CH$_2$—Phe |
| —(CH$_2$)$_3$—Me | —Me | —CHMeCH$_2$Me | —me | —CHMeCH$_2$Me | —Me |
| —CHMe$_2$ | —Me | —CHMe$_2$ | —Me | —CHMe$_2$ | —Me |
| —CH$_2$—Me | —Me | —CH$_2$—Me | —Me | —CH$_2$—Me | —Me |
| —(CH$_2$)$_3$—Me | —Me | —(CH$_2$)$_3$—Me | —Me | —(CH$_2$)$_3$—Me | —Me |
| —(CH$_2$)$_3$—Me | —Me | —(CH$_2$)$_3$—Me | —Me | —(CH$_2$)$_3$—Me | —Me |
| —CH$_2$—CH=CH$_2$ | —Me | —CH$_2$—CH=CH$_2$ | —Me | —CH$_2$—CH=CH$_2$ | —Me |
| —CHMeCH$_2$Me | —Me | —CHMeCH$_2$Me | —Me | —CHMeCH$_2$Me | —CH$_2$—Me |
| —CHMeCH$_2$Me | —Me | —CHMeCH$_2$Me | —Me | —CHMeCH$_2$Me | —(CH$_2$)$_3$—Me |
| —CHMeCH$_2$Me | —Me | —CHMeCH$_2$Me | —Me | —CHMeCH$_2$Me | —(CH$_2$)$_3$—Me |
| —CHMeCH$_2$Me | —Me | —CHMeCH$_2$Me | —Me | —CH$_2$Me | —Me |
| —CHMeCH$_2$Me | —Me | —CHMeCH$_2$Me | —Me | —(CH$_2$)$_3$—Me | —Me |
| -Cyclohexyl | —Me | -Cyclohexyl | —Me | -Cyclohexyl | —Me |
| —CH$_2$CHMe$_2$ | -Cyclohexyl | —CH$_2$CHMe$_2$ | —Me | —CH$_2$CHMe$_2$ | -Cyclohexyl |
| —CH$_2$CHMe$_2$ | -Cyclohexyl | —CH$_2$CHMe$_2$ | —Me | —CH$_2$CHMe$_2$ | —Me |
| —CHMeCH$_2$Me | —CHMe$_2$ | —CHMeCH$_2$Me | —CHMe$_2$ | —CHMeCH$_2$Me | —Me |
| —CH$_2$—Phe | —Me | —CH$_2$—Phe | —Me | —CH$_2$—Phe | —Me |
| -Cyclohexyl | —Me | -Cyclohexyl | —Me | -Cyclohexyl | —Me |
| —CHMe$_2$ | —CHMe$_2$ | —CHMe$_2$ | —Me | —CHMe$_2$ | —Me |
| —CHMe$_2$ | —CHMe$_2$ | —CHMe$_2$ | —CHMe$_2$ | —CHMe$_2$ | —Me |

$$\text{(IIb)}$$

| R¹ | R² | R³ | R⁴ | R⁵ | R⁶ |
|---|---|---|---|---|---|
| —CH₂—Me | —CHMe₂ | —CH₂Me | —Me | —CH₂—Me | —Me |
| —CH₂—Me | —CHMe₂ | —CH₂Me | —CHMe₂ | —CH₂—Me | —Me |
| —(CH₂)₃—Me | —CHMe₂ | —(CH₂)₃—Me | —Me | —(CH₂)₃—Me | —Me |
| —(CH₂)₃—Me | —CHMe₂ | —(CH₂)₃—Me | —CHMe₂ | —(CH₂)₃—Me | —Me |
| —(CH₂)₃—Me | —CHMe₂ | —(CH₂)₃—Me | —Me | —(CH₂)₃—Me | —Me |
| —(CH₂)₃—Me | —CHMe₂ | —(CH₂)₃—Me | —CHMe₂ | —(CH₂)₃—Me | —Me |
| —CH₂—CH=CH₂ | —CHMe₂ | —CH₂—CH=CH₂ | —Me | —CH₂—CH=CH₂ | —Me |
| —CH₂—CH=CH₂ | —CHMe₂ | —CH₂—CH=CH₂ | —CHMe₂ | —CH₂—CH=CH₂ | —Me |
| —Me | —Me | —CHMeCH₂Me | —Me | —CHMeCH₂Me | —Me |
| —H | —Me | —Me | —Me | —CHMeCH₂Me | —Me |
| —CH₂Me | —Me | —Me | —Me | —CHMeCH₂Me | —Me |
| —(CH₂)₃—Me | —Me | —Me | —Me | —CHMeCH₂Me | —Me |
| —CHMe₂ | —Me | —Me | —Me | —CHMeCH₂Me | —Me |
| —(CH₂)₃—Me | —Me | —Me | —Me | —CHMeCH₂Me | —Me |
| —CH₂CHMe₂ | —Me | —Me | —Me | —CHMeCH₂Me | —Me |

Me = methyl; Phe = phenyl

Coupling reagents which can be used for carrying out process b are all those which are suitable for producing an amide linkage (cf. for example: Houben-Weyl, Methoden der organischen Chemie [Methods in Organic Chemistry], Volume 15/2; Bodanszky et al., Peptide Synthesis 2nd ed. (Wiley & Sons, New York 1976) or Gross, Meienhofer, The Peptides: Analysis synthesis, biology (Academic Press, New York 1979). The following methods are preferably used: active ester method using pentachlorophenol (Pcp) and pentafluorophenol (Pfp), N-hydroxysuccinimide, N-hydroxy-5-norbornene-2,3-dicarboxamide (HONB), 1-hydroxybenzotriazole (HOBt) or 3-hydroxy-4-oxo-3,4-dihydro-1,2,3-benzotriazine as alcohol component, coupling with carbodiimides, such as dicyclohexylcarbodiimide (DCC) by the DCC additive process, or with N-propanephosphonic anhydride (PPA) and mixed anhydride method using pivaloyl chloride, ethyl chloroformate (EEDQ) and isobutyl chloroformate (IIDQ), or coupling with phosphonium reagents, such as benzotriazol-1-yl-oxy-tris(dimethylaminophosphonium) hexafluorophosphate (BOP), bis(2-oxo-3-oxazolidinyl)phosphinic chloride BOP-Cl), or with phosphonic ester reagents, such as diethyl cyanophosphonate (DEPC) and diphenylphosphoryl azide (DPPA) or uronium reagents, such as 2-(1H-benzotriazol-1-yl)-1,1,3,3-tetramethyluroniumtetrafluoro-borate (TBTU).

Coupling with phosphonium reagents, such as bis(2-oxo-3-oxazolidinyl)-phosphinic chloride (BOP-Cl), benzotriazol-1-yl-oxy-tris(dimethylamino-phosphonium) hexafluorophosphate (BOP) and phosphonic ester reagents, such as diethyl cyanophosphonate (DEPC) or diphenylphosphoryl azide (DPPA), is preferred.

Basic reaction auxiliaries which can be used for carrying out process b are the tertiary amines mentioned in process a, in particular trialkylamines, such as triethylamine, N,N-diisopropylethylamine or N-methylmorpholine.

Diluents which are used for carrying out process b are the halogenated hydrocarbons mentioned in process a, in particular chlorohydrocarbons.

Process b is carried out by combining compounds of the formula (II) in the presence of one of the above-mentioned coupling reagents and in the presence of a basic reaction auxiliary in a diluent under high-dilution conditions and stirring the mixture. The reaction time is 4 to 72 hours. The reaction is carried out at temperature between −5° C. and +100° C., preferably between −5° C. and +50° C., particularly preferably at 0° C. to room temperature. The process is carried out under atmospheric pressure.

For carrying out process b according to the invention, 1.0 to 3.0 mol, preferably 1.0 to 1.5 mol, of coupling reagent is generally used per mol of N-methyl-L-isoleucyl-D-lactyl-N-methyl-L-isoleucyl-D-lactyl-N-methyl-L-isoleucyl-D-lactic acid of the formula (II).

When the reaction is complete, the reaction solution is washed until weakly alkaline, and the organic phase is separated off, dried and concentrated in vacuo. The products obtained can be purified in the customary manner by recrystallization, distillation in vacuo or column chromatography.

The open-chain depsipeptides which are used as starting compounds can be prepared by processes known per se, for example the process described by H. -G. Lerchen and H. Kunz (Tetrahedron Lett. 26 (43) (1985) pp. 5257–5260; 28 (17) (1987) pp. 1873–1876) utilizing the esterification method described by B. F. Gisin (Helv. Chim. Acta 56 (1973) p. 1476).

The cyclic depsipeptides having 24 ring atoms include compounds of the general formula (Ia)

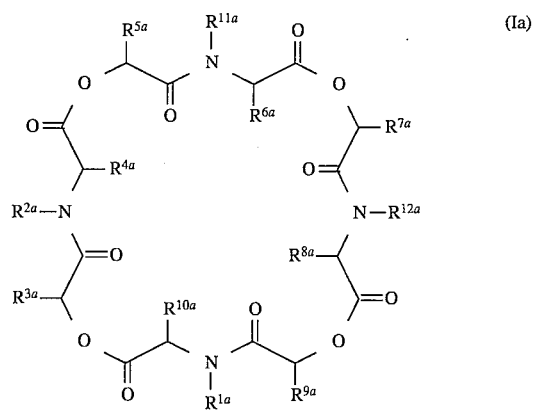

in which $R^{1a}$, $R^{2a}$, $R^{11a}$ and $R^{12a}$ independently of one another represent $C_{1-8}$-alkyl, $C_{1-8}$-halogenalkyl, $C_{3-6}$-cycloalkyl, aralkyl and aryl, $R^{3a}$, $R^{5a}$, $R^{7a}$ and $R^{9a}$ independently of one another represent hydrogen or straight-chain or branched $C_{1-8}$- alkyl which can optionally be substituted by hydroxyl, $C_{1-4}$-alkoxy, carboxyl,

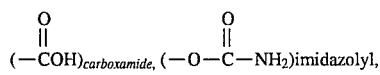

indolyl, guanidino, —SH or $C_{1-4}$-alkylthio, and furthermore represent aryl or aralkyl, each of which can be substituted by halogen, hydroxyl, $C_{1-4}$-alkyl or $C_{1-4}$-alkoxy, $R^{4a}$, $R^{6a}$, $R^{8a}$ and $R^{10a}$ independently of one another represent hydrogen, straight-chain $C_{1-5}$-alkyl, $C_{2-6}$-alkenyl, $C_{3-7}$-cycloalkyl, each of which can optionally be substituted by hydroxyl, $C_{1-4}$-alkoxy, carboxyl, carboxamide, imidazolyl, indolyl, guanidino, SH or $C_{1-4}$-alkylthio, and also represent aryl or aralkyl, each of which can be substituted by halogen, hydroxyl, $C_{1-4}$-alkyl or $C_{1-4}$-alkoxy, and their optical isomers and racemates.

Preferred compounds of the formula (Ia) which are employed are those in which $R^{1a}$, $R^{2a}$, $R^{11a}$ and $R^{12a}$ independently of one another represent methyl, ethyl, propyl, isopropyl, n-, s-, t-butyl or phenyl which is optionally substituted by halogen, $C_{1-4}$-alkyl, OH or $C_{1-4}$-alkoxy or represent benzyl or phenylethyl, each of which can optionally be substituted by the radicals indicated for phenyl; and $R^{3a}$ to $R^{10a}$ have the above-mentioned meaning.

Particularly preferred compounds of the formula (Ia) are those in which $R^{1a}$, $R^{2a}$, $R^{11a}$ and $R^{12a}$ independently of one another represent methyl, ethyl, propyl, isopropyl or n-, s- or t-butyl, $R^{3a}$, $R^{5a}$, $R^{7a}$ and $R^{9a}$ represent hydrogen, straight-chain or branched $C_{1-8}$-alkyl, in particular methyl, ethyl, propyl, i-propyl and n-, s- or t-butyl, each of which can optionally be substituted by $C_{1-4}$-alkoxy, in particular methoxy, ethoxy, imidazolyl, indolyl or $C_{1-4}$-alkylthio, in particular methythio and ethylthio, furthermore represent phenyl, benzyl or phenethyl, each of which can optionally be substituted by halogen, in particular chlorine; and $R^{4a}$, $R^{6a}$, $R^{8a}$ and $R^{10a}$ independently of one another represent hydrogen, methyl, ethyl, n-propyl, n-butyl, vinyl or cyclohexyl, each of which can optionally be substituted by methoxy, ethoxy, imidazolyl, indolyl, methylthio or ethylthio, and also represent isopropyl and s-butyl and furthermore phenyl, benzyl or phenylethyl, each of which is optionally substituted by halogen.

The compounds of the formula (Ia) can be prepared by subjecting open-chain octadepsipeptides of the formula (IIc)

in which $R^{1a}$ to $R^{12a}$ have the above-mentioned meaning to a cyclization reaction in the presence of a diluent and in the presence of a coupling reagent.

Suitable coupling reagents are all those compounds which are suitable for forming an amide linkage (cf. for example: Houben-Weyl, Methoden der organischen Chemie [Methods in Organic Chemistry], Volume 15/2; Bodanszky et al., Peptide Synthesis 2nd Ed. (Wiley/Sons, New York 1976).

The following reagents and methods are preferably suitable: active ester method using pentafluorophenol (Pfp), N-hydroxysuccinimide, 1-hydroxybenzotriazole, coupling with carbodiimides, such as dicyclohexylcarbodiimide or N'-(3-dimethylaminopropyl)-N-ethylcarbodiimide (Ebc), and the mixed anhydride method, or coupling with phosphonium reagents, such as benzotriazol-1-yl-oxy-tris(dimethylaminophosphonium) hexafluorophosphate (BOP), bis(2-oxo-3-oxazolidinyl)-phosphinic chloride (BOP-Cl), or with phosphonic ester reagents, such as diethyl cyanophosphonate (DEPC) and diphenylphospharyl azide (DPPA).

Coupling with bis(2-oxo-3-oxazolidinyl)-phosphinic chloride (BOP-Cl) and N'-(3-dimethylaminopropyl)-N-ethylcarbodiimide (EDC) in the presence of 1-hydroxybenzotriazole (HOBt) is particularly preferred.

The reaction is carried out at temperatures of 0°–150° C., preferably at 20° to 100° C., particularly preferably at room temperature.

Suitable diluents are all inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, furthermore ethers, such as diethyl ether, dibutyl ether, glycol dimethyl ether and diglycol dimethyl ether, tetrahydrofuran and dioxane, furthermore ketones, such as acetone, methyl ethyl ketone, methyl isopropyl ketone and methyl isobutyl ketone, furthermore esters, such as methyl acetate and ethyl acetate, furthermore nitriles, such as, for example, acetonitrile and propionitrile, benzonitrile and glutaronitrile, and additionally amides, such as, for example, dimethylformamide, dimethylacetamide and N-methylpyrrolidone, and also dimethyl sulphoxide, tetramethylene sulphone and hexamethylphosphoric triamide.

The compounds of the formula (IIc) and the coupling reagents are employed in the ratio of 1:1 to 1:1.5 to each other. An approximately equimolar ratio is preferred.

When the reaction is complete, the diluent is distilled off, and the compounds of the formula (Ia) are purified in the customary manner, for example by chromatography.

The open-chain octadepsipeptides of the formula (IIc)

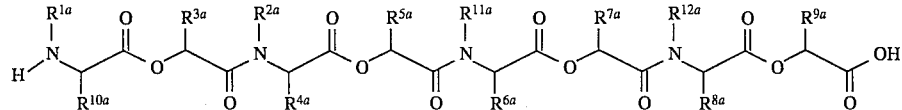

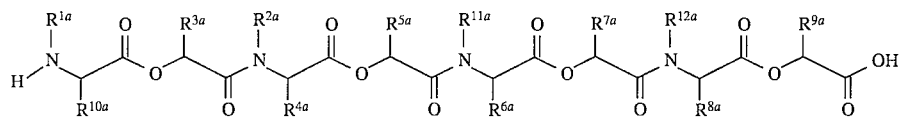   (IIc)

in which the radicals have the above-mentioned meanings are obtained by subjecting compounds of the formula (IIIa)

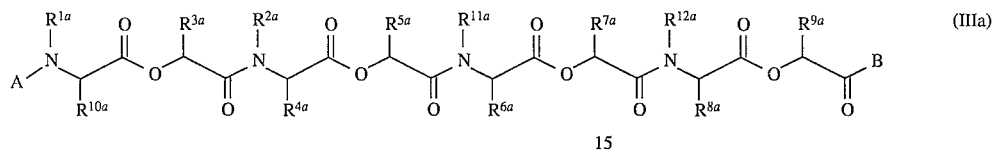   (IIIa)

in which

A represents benzyl and

B represents OH and $R^{1a}$ to $R^{12a}$ have the above-mentioned meaning to a hydrogenolysis reaction in the presence of a diluent and of a catalyst.

The compounds of the formula (IIIa)

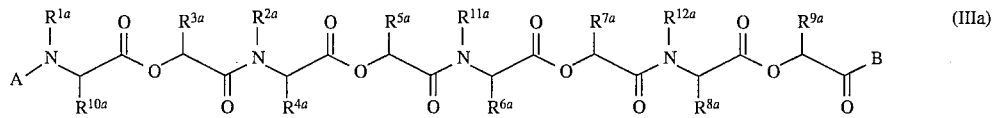   (IIIa)

in which the radicals have the above-mentioned meaning are obtained by subjecting compounds of the formula (IVa)

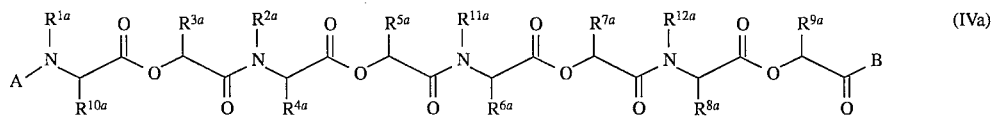   (IVa)

in which the radicals have the above-mentioned meaning to a hydrolysis reaction.

Compounds of the formula (IVa) and their stereoisomers are obtained by subjecting tetradepsipeptides of the formula (Va)

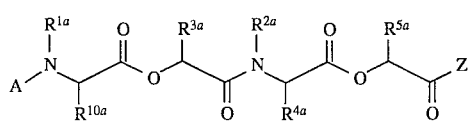   (Va)

in which

A represents benzyl and

Z represents OH and $R^{1a}$, $R^{2a}$, $R^{3a}$, $R^{4a}$, $R^{5a}$ and $R^{10a}$ have the above-mentioned meaning and tetradepsipeptides of the formula (VIa)

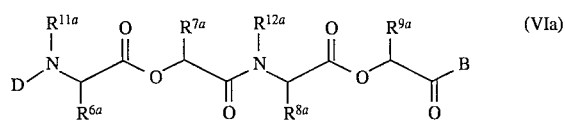   (VIa)

in which

D represents hydrogen and

B represents tert-butoxy and $R^{6a}$, $R^{7a}$, $R^{8a}$, $R^{9a}$, $R^{11a}$ and $R^{12a}$ have the above-mentioned meaning to a condensation reaction in the presence of a diluent and of a coupling reagent.

Tetradepsipeptides of the formula (Va) are obtained by hydrolyzing tetradepsipeptides of the formula (VIIa)

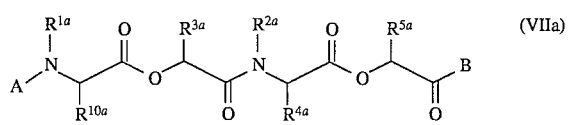   (VIIa)

in which

A represents benzyl and

B represents tert-butoxy and $R^{1a}$, $R^{2a}$, $R^{3a}$, $R^{4a}$, $R^{5a}$ and $R^{10a}$ have the above-mentioned meaning in the presence of a diluent and of a protonic acid.

Tetradepsipeptides of the formula (VIa)

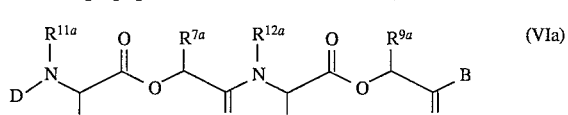   (VIa)

in which

D represents hydrogen and

B represents tert-butoxy and the remaining radicals have the above-mentioned meaning are obtained by subjecting tetradepsipeptides of the formula (VIIa)

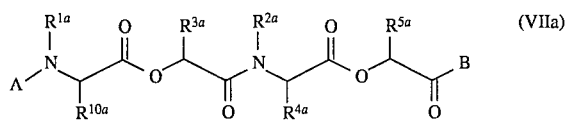

in which

A represents benzyl and

B represents tert-butoxy and $R^{1a}$, $R^{2a}$, $R^{3a}$, $R^{4a}$, $R^{5a}$ and $R^{10a}$ have the above-mentioned meaning to a hydrogenolysis reaction in the presence of a diluent and of a catalyst.

Tetradepsipeptides of the formula (VIIa) are obtained by subjecting didepsipeptides of the formula (VIIIa)

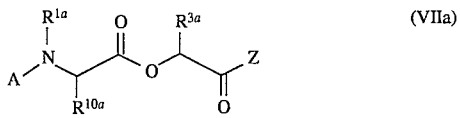

in which

A represents benzyl and

Z represents OH and $R^{1a}$, $R^{3a}$ and $R^{10a}$ have the above-mentioned meaning and didepsipeptides of the formula (IXa)

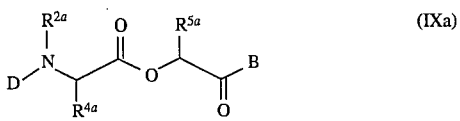

in which

D represents hydrogen and

B represents tert-butoxy and $R^{2a}$, $R^{4a}$ and $R^{5a}$ have the above-mentioned meaning to a condensation reaction in a diluent in the presence of a coupling reagent.

While having low toxicity to warm-blooded species, the compositions according to the invention are suitable for combating pathogenic endoparasites which occur in humans and in animal keeping and livestock breeding in productive livestock, breeding animals, zoo animals, laboratory animals, experimental animals and pets. In this context, they are active against all or individual stages of development of the pests and against resistant and normally-sensitive species. By combating the pathogenic endoparasites, it is intended to reduce disease, deaths and decreasing performance (for example in the production of meat, milk, wool, hides, eggs, honey etc.), so that more economical and simpler animal keeping is possible by using the active compounds. The pathogenic endoparasites include Cestodes, Trematodes, Nematodes and Acantocephala, in particular:

From the order of the Pseudophyllidea, for example: Diphyllobothrium spp., Spirometra spp., Schistocephalus spp., Ligula spp., Bothridium spp., Diphlogonoporus spp.

From the order of the Cyclophyllidea, for example: Mesocestoides spp., Anoplocephala spp., Paranoplocephala spp., Moniezia spp., Thysanosomsa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Echinocotyle spp., Diorchis spp., Dipylidium spp., Joyeuxiella spp., Diplopylidium spp.

From the subclass of the Monogenea, for example: Gyrodactylus spp., Dactylogyrus spp., Polystoma spp.

From the subclass of the Digenea, for example: Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp., Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp. Metorchis spp., Heterophyes spp., Metagonimus spp.

From the order of the Enoplida, for example: Trichuris spp., Capillaria spp., Trichomosoides spp., Trichinella spp.

From the order of the Rhabditia, for example: Micronema spp., Strongyloides spp.

From the order of the Strongylida, for example: Stronylus spp., Triodontophorus spp., Oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp..

From the order of the Oxyurida, for example: Oxyuris spp., Enterobius spp., Passalurus spp., Syphacia spp., Aspiculuris spp., Heterakis spp..

From the order of the Ascaridia, for example: Ascaris spp., Toxascaris spp., Toxocara spp., Parascaris spp., Anisakis spp., Ascaridia spp..

From the order of the Spirurida, for example: Gnathostoma spp., Physaloptera spp., Thelazia spp., Gongylonema spp., Habronema spp., Parabronema spp., Draschia spp., Dracunculus spp..

From the order of the Filariida, for example: Stephanofilaria spp., Parafilaria spp., Setaria spp., Loa spp., Dirofilaria spp., Litomosoides spp., Brugia spp., Wuchereria spp., Onchocerca spp..

From the order of the Gigantorhynchida, for example: Filicollis spp., Moniliformis spp., Macracanthorhynchus spp., Prosthenorchis spp..

The productive livestock and breeding animals include mammals such as, for example, cattle, horses, sheep, pigs, goats, camels, water buffalo, donkeys, rabbits, fallow deer, reindeer, fur-bearing animals such as, for example, minks, chinchilla, racoon, birds such as, for example, chickens, geese, turkeys, ducks, ostriches, freshwater and salt-water fish such as, for example, trout, carps, eels, reptiles, insects such as, for example, honeybee and silkworm.

Laboratory animals and experimental animals include mice, rats, guinea pigs, golden hamsters, dogs and cats.

Pets include dogs and cats.

The active compounds can be administered prophylactically as well as therapeutically.

The active compounds, directly or in the form of suitable preparations, are administered, enterally, parenterally, dermally, nasally, by environment treatment, or with the aid of active-compound-containing shaped articles such as, for example, strips, plates, bands, collars, ear marks, limb bands, marking devices.

The active compounds are administered enterally, for example orally, in the form of powders, tablets, capsules, pastes, drinks, granules, or solutions, suspensions and emulsions which can be administered orally, or boli, medicated feed or drinking water. Dermal administration is effected, for example in the form of dipping, spraying or pouring-on and spotting-on. Parenteral administration is effected, for example, in the form of injection (intramuscularly, subcutaneously, intravenously, intraperitoneally or by implants.

Suitable preparations are:

Solutions such as injectable solutions, oral solutions, concentrates for oral administration after dilution, solutions for use on the skin or in body cavities, pour-on and spot-on formulations, gels;

Emulsions and suspension for oral or dermal administration and for injection; semi-solid preparations;

Formulations in which the active compound is incorporated in a cream base or in an oil-in-water or water-in-oil emulsion base;

Solid preparations such as powders, premixes or concentrates, granules, pellets, tablets, boli, capsules; aerosols and inhalants, shaped articles containing active compound.

Injectable solutions are administered intravenously, intramuscularly and subcutaneously.

Injectable solutions are prepared by dissolving the active compound in a suitable solvent and, if appropriate, adding additives such as solubilizers, acids, bases, buffer salts, antioxidants and preservatives. The solutions are sterile-filtered and drawn off.

The following may be mentioned as solvents: physiologically acceptable solvents such as water, alcohols such as ethanol, butanol, benzyl alcohol, glycerol, propylene glycol, polyethylene glycols, N-methyl-pyrrolidone, and mixtures of these.

If appropriate, the active compounds can also be dissolved in physiologically acceptable vegetable or synthetic oils which are suitable for injection.

The following may be mentioned as solubilizers: solvents which enhance solution of the active compound in the main solvent, or which prevent its precipitation. Examples are polyvinylpyrrolidone, polyoxyethylated castor oil, polyoxyethylated sorbitan esters.

Preservatives are: benzyl alcohol, trichlorobutanol, p-hydroxybenzoic esters, n-butanol.

Oral solutions are administered directly. Concentrates are administered orally after previously having been diluted to the administration concentration. Oral solutions and concentrates are prepared as described above in the case of the injectable solutions, it being possible to dispense with working under sterile conditions.

Solutions for use on the skin are applied dropwise, brushed on, rubbed in, splashed on or sprayed on. These solutions are prepared as described above in the case of injectable solutions.

It may be advantageous to add thickeners during the preparation. Thickeners are: inorganic thickeners such as bentonite, colloidal silica, aluminium monostearate, organic thickeners such as cellulose derivatives, polyvinyl alcohols and their copolymers, acrylates and metacrylates.

Gels are applied to, or brushed on, the skin, or introduced into body cavities. Gels are prepared by treating solutions which have been prepared as described in the case of the injectable solutions with such an amount of thickener that a clear substance of cream-like consistency is formed. Thickeners employed are the thickeners indicated further above.

Pour-on and spot-on formulations are poured onto, or splashed onto, limited areas of the skin, the active compound penetrating the skin and acting systematically.

Pour-on and spot-on formulations are prepared by dissolving, suspending or emulsifying the active compound in suitable solvents or solvent mixtures which are tolerated by the skin. If appropriate, other adjuvants such as colourants, resorption accelerators, antioxidants, light stabilizers, and tackifiers are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, aromatic and/or aliphatic hydrocarbons, vegetable or synthetic oils, DMF, dimethylacetamide, N-methylpyrrolidone, 2,2-dimethyl-4-oxy-methylene-1,3-dioxolane.

Colourants are all colourants which are licensed for use on animals and which can be dissolved or suspended.

Examples of resorption accelerators are DMSO, spreading oils such as isopropyl myristate, dipropylene glycol pelargonate, silicone oils, fatty acid esters, triglycerides, fatty alcohols.

Antioxidants are sulphites or metabisulphites such as potassium metabisulphite, ascorbic acid, butylhydroxytoluene, butylhydroxyanisole, tocopherol.

Examples of light stabilizers are novantisolic acid.

Examples of tackifiers are cellulose derivatives, starch derivatives, polyacrylates, natural polymers such as alginates, gelatine.

Emulsions can be administered orally, dermally or in the form of injections.

Emulsions are either of the water-in-oil type or of the oil-in-water type.

They are prepared by dissolving the active compound either in the hydrophobic or in the hydrophilic phase and homogenising this phase with the solvent of the other phase, with the aid of suitable emulsifiers and, if appropriate, other adjuvants such as colourants, resorption accelerators, preservatives, antioxidants, light stabilizers, viscosity-increasing substances.

The following may be mentioned as the hydrophobic phase (oils): paraffin oils, silicone oils, natural vegetable oils such as sesame seed oil, almond oil, castor oil, synthetic triglycerides such as caprylic/capric acid biglyceride, triglyceride mixture with vegetable fatty acids of chain length $C_{8-12}$ or with other specifically selected natural fatty acids, partial glyceride mixtures of saturated or unsaturated fatty acids which may also contain hydroxyl groups, and mono- and diglycerides of the $C_8/C_{10}$-fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16}$–$C_{18}$, isopropyl myristate, isopropyl palmitate, caprylic/capric esters of saturated fatty alcohols of chain length $C_{12}$–$C_{18}$, isopropyl stearate, oleyl oleate, decyl oleate, ethyl oleate, ethyl lactate, waxy fatty acid esters such as artificial uropygial gland fat from ducks, dibutyl phthalate, diisopropyl adipate, ester mixtures related to the latter, etc.

Fatty alcohols such as isotridecyl alcohol, 2-octyldodecanol, cetylstearyl alcohol, oleyl alcohol.

Fatty acids such as, for example, oleic acid and its mixtures.

The following may be mentioned as hydropholic phase: water, alcohols such as, for example, propylene glycol, glycerol, sorbitol and their mixtures.

The following may be mentioned as emulsifiers: nonionic surfactants, for example polyoxyethylated castor oil, polyoxyethylated sorbitan monooleate, sorbitan monostearate, glycerol monostearate, polyoxyethyl stearate, alkylphenol polyglycol ethers;

ampholytic surfactants such as disodium N-lauryl-β-iminodipropionate or lecithin;

anionic surfactants such as sodium lauryl sulphate, fatty alcohol ether sulphates, the monoethanol amine salt of mono/dialkyl polyglycol ether orthophosphoric acid esters;

cationic surfactants such as cetyltrimethylammonium chloride.

The following may be mentioned as other adjuvants: viscosity-increasing substances and substances which stabilise the emulsion, such as carboxymethylcellulose, methylcellulose and other cellulose and starch derivatives, polyacrylates, alginates, gelatine, gum arabic, polyvinylpyrrolidone, polyvinyl alcohol, copolymers of methyl vinyl ether and maleic anhydride, polyethylene glycols, waxes, colloidal silica, or mixtures of the substances mentioned.

Suspensions can be administered orally, dermally or in the form of injection. They are prepared by suspending the active substance in an excipient liquid, if appropriate with the addition of further adjuvants such as wetting agents, colourants, resorption accelerators, preservatives, antioxidants light stabilizers.

Excipient liquids which may be mentioned are all homogeneous solvents and solvent mixtures.

Wetting agents (dispersants) which may be mentioned are the surfactants indicated further above.

Further adjuvants which may be mentioned are those indicated further above.

Semi-solid preparations can be administered orally or dermally. They are only distinguished from the above-described suspensions and emulsions by their higher viscosity.

To prepare solid preparations, the active compound is mixed with suitable excipients, if appropriate with the addition of adjuvants, and the mixture is formulated as desired.

Excipients which may be mentioned are all physiologically acceptable solid inert substances. Suitable as such are inorganic and organic substances. Examples of inorganic substances are sodium chloride, carbonates such as calcium carbonate, hydrogencarbonates, aluminium oxides, silicas, clays, precipitated or colloidal silica, and phosphates.

Examples of organic substances are sugars, cellulose, food and animal feeds such as dried milk, carcass meals, cereal meals and coarse cereal meals and starches.

Adjuvants are preservatives, antioxidants and colourants which have already been indicated further above.

Other suitable adjuvants are lubricants and gliding agents such as, for example, magnesium stearate, stearic acid, talc, bentonites, disintegrants such as starch or crosslinked polyvinylpyrrolidone, binders such as, for example, starch, gelatine or linear polyvinylpyrrolidone, and also dry binders such as microcrystalline cellulose.

In the preparations, the active compounds can also be present in the form of a mixture with synergists or with other active compounds which act against pathogenic endoparasites. Examples of such active compounds are L-2,3,5,6-tetrahydro-6-phenyl-imidazothiazole, benzimidazole carbamates, pyrantel.

Ready-to-use preparations contain the active compounds in concentrations of 10 ppm–20 percent by weight, preferably 0.1–10 percent by weight.

Preparations which are diluted prior to administration contain the active compounds in concentrations of 0.5–90% by weight, preferably 5 to 50 percent by weight.

In general, it has proved advantageous to administer amounts of the mixture according to the invention of approximately 10 to approximately 100 mg of active compound per kg of body weight per day, to achieve effective results. 10 to 50 mg of active compound mixture per kg of body weight are preferred.

In general, the ratio by weight of praziquantel, or epsiprantel, to depsipeptide in the compositions is 1:1 to 10, preferably 1:1 to 2, very particularly preferably 1:1.

EXAMPLE A

In Vivo Nematode Test

Ancylostoma caninum in dogs

Beagle puppies are infected experimentally with hookworms, species Ancylostoma caninum. To infect the dogs, A. caninum is applied orally in the form of 250 $L_3$ larvae.

After the prepatent period has elapsed (or during the prepatent period if an antilarval activity is detected), the active compounds are administered orally in the form of the pure active compound in gelatine capsules.

The activity is evaluated by two methods.

1. The worm eggs excreted with the faeces are counted before and after the treatment.
2. The percentage activity in the critical test using the formula:

$$\% \text{ activity} = \frac{\text{Worms excreted after the treatment}}{\text{Worms excreted after the treatment plus remaining worms}} \times 100$$

In the Table which follows, the dosage (mg/kg) is indicated, at which an activity of 100% was achieved by both evaluation methods.

TABLE A

| Active compound | Dosis effective [mg/kg] |
| --- | --- |
| Cyclo(—MeLeu—D—Lac—MeLeu—D—PhLac—MeLeu—D—Lac—MeLeu—D—PhLac—) [PF 1022] | 1 |
| 2-(Cyclohexylcarbonyl)-1,2,3,6,7,11b-hexahydro-4H-pyrazino[2,1-a]isoquinolin-4-one [Praziquantel] | 0 |
| 2-(Cyclohexylcarbonyl)-2,3,6,7,8,12b-hexahydro-pyrazino[2,1-a][2]benzazepin-4(1H)-one [Epsiprantel] | 0 |

TABLE A-continued

| Active compound | Dosis effective [mg/kg] |
|---|---|
| Cyclo(—MeLeu—D—Lac—MeLeu—D—PhLac—MeLeu—D—Lac—MeLeu—D—PhLac—) [PF 1022] + 2-(Cyclohexylcarbonyl)-1,2,3,6,7,11b-hexahydro-4H-pyrazino[2,1-a]isoquinolin-4-one [Praziquantel] (1:1) | 0,5 |
| Cyclo(—MeLeu—D—Lac—MeLeu—D—PhLac—MeLeu—D—Lac—MeLeu—D—PhLac—) [PF 1022] + 2-(Cyclohexylcarbonyl)-2,3,6,7,8,12b-hexahydro-pyrazino[2,1-a][2]benzazepin-4(1H)-one [Epsiprantel] (1:1) | 0,5 |
| Cyclo(—MeLeu—D—Lac—MeLeu—D-p-MorPhLac—MeLeu—D—Lac—MeLeu—D-p-MorPhLac—) | 0,5 |
| Cyclo(—MeLeu—D—Lac—MeLeu—D-p-MorPhLac—MeLeu—D—Lac—MeLeu—D-p-MorPhLac—) + 2-(Cyclohexylcarbonyl)-1,2,3,6,7,11b-hexahydro-4H-pyrazino[2,1-a]isoquinolin-4-one [Praziquantel] (1:1) | 0,25 |
| Cyclo(—MeLeu—D—Lac—MeLeu—D-p-MorPhLac—MeLeu—D—Lac—MeLeu—D-p-MorPhLac—) + 2-(Cyclohexylcarbonyl)-2,3,6,7,8,12b-hexahydro-pyrazino[2,1-a][2]benzazepin-4(1H)-one [Epsiprantel](1:1) | 00,25 |

MeLeu: N-methyl-L-leucine; D—Lac: D-lactic acid; D—PhLac: D-β-phenyllactic acid; D-p-MorPhLac: D-β-p-morpholino-phenyllactic acid

EXAMPLE B

In Vivo Nematode Test

Ancylostoma tubaeforme in cats

Kittens are infected experimentally with $L_3$ larvae of hookworms, species Ancylostoma tubaeforme. For the infection, 250 larvae are applied orally, or about 500 cutaneously.

After the prepatent period has elapsed (or during the prepatent period if an antilarval activity is detected), the active compounds are administered orally in the form of the pure active compound in gelantine capsules.

The activity is evaluated by two methods.

1. The worm eggs excreted with the faeces are counted before and after the treatment.

2. The percentage activity in the critical test using the formula:

$$\% \text{ activity} = \frac{\text{Worms excreted after the treatment}}{\text{Worms excreted after the treatment plus remaining worms}} \times 100$$

In the Table B which follows, the dosage (mg/kg) is indicated, at which an activity of 100% was achieved by both evaluation methods:

TABLE B

| Active compound | Dosis effective [mg/kg] |
|---|---|
| Cyclo(—MeLeu—D—Lac—MeLeu—D—PhLac—MeLeu—D—Lac—MeLeu—D—PhLac—) [PF 1022] | 1 |
| 2-(Cyclohexylcarbonyl)-1,2,3,6,7,11b-hexahydro-4H-pyrazino[2,1-a]isoquinolin-4-one [Praziquantel] | 0 |
| 2-(Cyclohexylcarbonyl)-2,3,6,7,8,12b-hexahydro-pyrazino[2,1-a][2]benzazepin-4(1H)-one [Epsiprantel] | 0 |
| Cyclo(—MeLeu—D—Lac—MeLeu—D—PhLac—MeLeu—D—Lac—MeLeu—D—PhLac—) [PF 1022] + 2-(Cyclohexylcarbonyl)-1,2,3,6,7,11b-hexahydro-4H-pyrazino[2,1-a]isoquinolin-4-one [Praziquantel] (1:1) | 0,5 |
| Cyclo(—MeLeu—D—Lac—MeLeu—D—PhLac—MeLeu—D—Lac—MeLeu—D—PhLac—) [PF 1022] + 2-(Cyclohexylcarbonyl)-2,3,6,7,8,12b-hexahydro-pyrazino[2,1-a][2]benzazepin-4(1H)-one [Epsiprantel] (1:1) | 0,5 |
| Cyclo(—MeLeu—D—Lac—MeLeu—D-p-MorPhLac—MeLeu—D—Lac—MeLeu—D-p-MorPhLac—) | 0,5 |
| Cyclo(—MeLeu—D—Lac—MeLeu—D-p-MorPhLac—MeLeu—D—Lac—MeLeu—D-p-MorPhLac—) + 2-(Cyclohexylcarbonyl)-1,2,3,6,7,11b-hexahydro-4H-pyrazino[2,1-a]isoquinolin-4-one [Praziquantel] (1:1) | 0,25 |
| Cyclo(—MeLeu—D—Lac—MeLeu—D-p-MorPhLac—MeLeu—D—Lac—MeLeu—D-p-MorPhLac—) + 2-(Cyclohexylcarbonyl)-2,3,6,7,8,12b-hexahydro-pyrazino[2,1-a][2]benzazepin-4(1H)-one [Epsiprantel] (1:1) | 00,25 |

MeLeu: N-methyl-L-leucine; D—Lac: D-lactic acid; D—PhLac: D-β-phenyllactic acid; D-p-MorPhLac: D-β-p-morpholino-phenyllactic acid Examples of the preparation of the cyclic depsipeptides having 18 ring atoms:

EXAMPLE 1:

Cyclo(-N-methyl-L-isoleucyl-D-lactyl-N-methyl-L-isoleucyl-D-lactyl-N--methyl-L-isoleucyl-D-lactyl-)

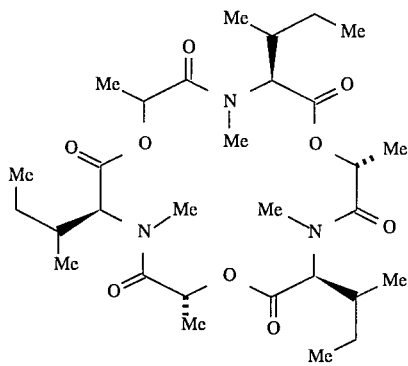

0.99 g (1.08 mmol) of Z-(-L-MeIle-D-Lac-)$_3$-O-Pfp in 50 ml of absolute dioxane are injected uniformly in the course of 6 hours at an internal temperature of 95° C. into a rapidly stirred suspension of 1.5 g of 10% palladium/charcoal in 550 ml of absolute dioxane containing 12 ml of ethanol and 160 mg (1.08 mmol) of 4-pyrrolidinopyridine. During this process, hydrogen is passed through the reaction solution. Stirring is then continued for a further 4 hours at 95° C. and for 12 hours at room temperature. The mixture is filtered, and the entire reaction batch is concentrated in vacuo. The colourless oily residue is taken up in chloroform and washed twice using 5% strength citric acid, twice using NaHCO$_3$ solution and twice using water. The organic phase is dried over sodium sulphate, and the solvent is subsequently distilled off in vacuo. The crude product which remains can be prepurified chromatographically over a silica gel column (silica gel 60-Merck, particle size: 0.04 to 0.063 mm) using toluene: ethyl acetate (4:1) as the eluant (purity 84%). This is followed by preparative HPLC purification. 710 mg (36.8% of theory) of cyclo(-N-methyl-L-isoleucyl-D-lactyl-N-methyl-L-isoleucyl-D-lactyl-N-methyl- L-isoleucyl-D-lactyl-) are obtained.

m.p.:210°–212 C.

$^1$H-NMR (400 MHz, CDCl$_3$, δ): 0.87 (t, 9H, —CH$_2$—C$\underline{H}_3$; J=7.3 Hz); 0.98; 1.44 (2d, 18H, —CH—C$\underline{H}_3$; J=6.5Hz; 1.35–1.41 (br. m, 3H, —C$\underline{H}$—CH$_3$); 2.02–2.04 (br. m, 6H, —C$\underline{H}_2$—CH$_3$); 3.03 (s, 9H, —N—C$\underline{H}_3$); 4.45 (m, 3H, N—C$\underline{H}$—CO); 5.57–5.62 (m, 3H, O—C$\underline{H}$—CO) ppm $^{13}$C-NMR (100 MHz, CDCl$_3$, δ): 10.9; 16.0; 16.6 (—$\underline{C}$H$_3$); 24.8 (—$\underline{C}$H$_2$—); 33.3 (—$\underline{C}$H—); 33.9 (—N—$\underline{C}$H$_3$); 61.9 (—N—$\underline{C}$H—); 66.4 (—O—$\underline{C}$H—); 169.3 (—$\underline{C}$O—N—); 169.9 (—$\underline{C}$O—O—) ppm FAB-MS m/z (%): 598 (M$^+$+H,12); 597 (37); 541 (42); 524 (14); 182 (100)

The compounds of the formula (I) listed in Table 1 below can be prepared analogously in the form of the LDLDLD stereoisomers.

Table 1

Examples of compounds of the general formula (I)

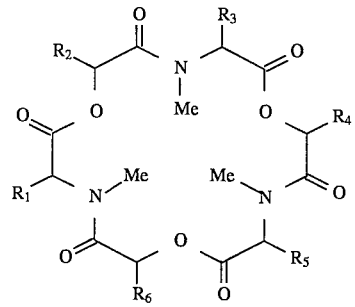

| Ex. No. | R$^1$ | R$^2$ | R$^3$ | R$^4$ | R$^5$ | R$^6$ | Physical Data$^{a)}$ |
|---|---|---|---|---|---|---|---|
| 2 | —CH$_2$CHMe$_2$ | —Me | —CH$_2$CHMe$_2$ | —Me | —CH$_2$CHMe$_2$ | —Me | 16,5; 21,9; 22,8 (C$\underline{H}_3$); 24,9(—$\underline{C}$H—); 32,0 (—N—$\underline{C}$H$_3$); 37,4(—$\underline{C}$H$_3$); 55,8 (—N—$\underline{C}$H—); 67,0(—O—$\underline{C}$H—); 169,4 (—$\underline{C}$O—N—); 170,5 (—$\underline{C}$O—O—) |
| 3 | —CH$_2$CHMe$_2$ | —Me | —CH$_2$CHMe$_2$ | —CH$_2$—Ph | —CH$_2$CHMe$_2$ | —Me | 16,4; 21,7; 21,8; 22,8; 22,9; 23,0 (—$\underline{C}$H$_3$); 24,6; 24,9(—$\underline{C}$H—); 31,0; 31,7; 32,8 (—N—$\underline{C}$H$_3$); 36,8; 37,4; 37,6(—$\underline{C}$H$_3$); 54,6; 55,3; 56,5(—O—$\underline{C}$H—); 67,0; 67,1; 70,2; (—O—$\underline{C}$H—); 168,8; 169,7(—$\underline{C}$O—N—); 170,3; 170,5; 170,6 (—$\underline{C}$O—O—) |
| 4 | —CHMeCH$_2$Me | —CHMe$_2$ | —CHMeCH$_2$Me | —CHMe$_2$ | —CH$_2$—Ph | —CHMe$_2$ | 15,7; 15,9; 18,2; 18,3(—$\underline{C}$H$_2$); 18,3; |

-continued

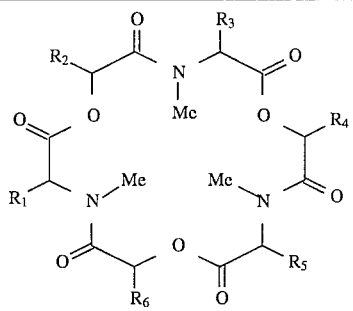

| Ex. No. | R¹ | R² | R³ | R⁴ | R⁵ | R⁶ | Physical Data[a] |
|---|---|---|---|---|---|---|---|
| | | | | | | | 18,6; 19,0; 25,0 (—$\underline{CH}_2$—); 25,2; 29,4; 29,7; 30,3(—$\underline{CH}$—); 31,4; 31,8, 36,0 (—N—$\underline{CH}_2$); 35,0(—$\underline{CH}_2$—Ph); 59,6; 60,5; 62,6(—N—$\underline{CH}$—); 74,8; 75,2(—O—$\underline{CH}$—); 126,6; 128,4; 129,1(arom.—$\underline{CH}$); 137,7(arom.—$\underline{C}$); 169,1; 169,2; 169,7; (—$\underline{CO}$—N—); 169,3; 170,3; 170,4(—$\underline{CO}$—O—) |
| 5 | —CHMeCH₂Me | —CHMe₂ | —CHMeCH₂Me | —Me | —CHMeCH₂Me | —Me | 10,3; 10,6; 11,4; 15,3; 15,8; 16,0; 16,7; 16,8; 18,0; 18,4; (—$\underline{CH}_2$); 24,4; 24,9; 25,0(—$\underline{CH}$—); 29,9; 32,3; 34,1; 34,7(—$\underline{CH}$—); 31,2; 31,6; 35,6(N—$\underline{CH}_2$); 59,5; 60,5; 65,1(N—$\underline{CH}$); 66,1; 67,5; 74,0(O—$\underline{CH}$—); 169,0; 169,1; ($\underline{CO}$—N) 169,8; 170,1; 170,6(—$\underline{CO}$—O) |
| 6 | —CH₂CHMe₂ | —Me | —CHMeCH₂Me | —Me | —CHMeCH₂Me | —Me | 10,6; 10,9; 15,7; 16,2; 16,5; 17,0; 21,8; 22,9; (—$\underline{CH}_2$); 24,4; 37,1(—$\underline{CH}_2$—); 24,8; 33,3; 34,4; (—$\underline{CH}$—); 31,0; 32,7; 33,0; (—N—$\underline{CH}_2$); 57,0; 60,0; 62,0; (—N—$\underline{CH}$—); 66,1; 66,6; 67,4; (—O—$\underline{CH}$—); 168,9; 169,3; 169,5; (—$\underline{CO}$—N—); 170,0; 170,5(—$\underline{CO}$—O) |
| 7 | —Me | —Me | —CHMeCH₂Me | —Me | —CHMeCH₂Me | —Me | 10,6; 10,7; 13,5; 15,4; 15,9; 16,0; 16,8; 17,1(—$\underline{CH}_2$); 24,4; 24,5(—$\underline{CH}$—); 30,9; 31,5(—$\underline{CH}$—); 32,5; 33,9; 34,2(—N—$\underline{CH}_2$); 56,2; 59,9; 60,5(—N—$\underline{CH}$—); 66,0; 66,3 67,7(—O—$\underline{CH}$—); 168,7; 169,7; 170,1(—$\underline{CO}$—N—); 169,0; 170,0; 170,4(—$\underline{CO}$—O—) |
| 8 | —Me | —Me | —CHMeCH₂Me | —Me | —H | —Me | 499(M⁺, 100); 428(38); 312(28°); 213(62); 182(73); 140°(49) |
| 9 | —Me | —Me | —CHMeCH₂Me | —Me | —Me | —Me | 31,8; 33,8; 34,6(—N—$\underline{CH}_2$) 168,1; 168,7; 169,9 (—$\underline{CO}$—N—); 170,0; 170,4; 170,5: (—$\underline{CO}$—O—); 513(M⁺, 42); 440(22); 255(29); 213(60); 182(75); 141(82); 58(100) |
| 10 | —Me | —Me | —CHMeCH₂Me | —Me | —CH₂CH₃—Me | —Me | 30,1; 33,9; 34,8(—M—$\underline{CH}_2$); 168,6; 168,7; 169,9 |

-continued

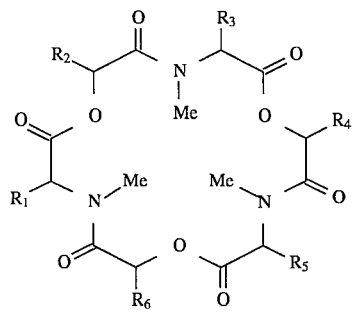

| Ex. No. | R¹ | R² | R³ | R⁴ | R⁵ | R⁶ | Physical Data[a] |
|---|---|---|---|---|---|---|---|
| | | | | | | | ($-\underline{C}O-N-$); 170,0, 170,3; 170,4($-\underline{C}O-O-$); 541(M87); 468(41); 354(18); 255(42); 213(41); 182(100); 141(90) |
| 11 | —Me | —Me | —CHMeCH₂Me | —Me | —CHMe | —Me | 30,9; 31,2; 33,9($-N-\underline{C}H_2$); 168,5; 168,6; 169,7 ($-\underline{C}O-N-$); 169,9; 170,1; 170,4($-\underline{C}O-O-$); 541(M⁺81); 468(39); 255(49); 213(36); 182(100); 141(68) |
| 12 | —Me | —Me | —CHMeCH₂Me | —Me | —CH₂—CHMe₂ | —Me | 29,9; 33,9; 34,9($-N-\underline{C}H_2$); 168,4; 168,7; 169,9 $-\underline{C}O-N-$); 170,0; 170,3; 170,5($-\underline{C}O-O$); 555(M⁺, 45); 499(49); 428(12); 255(40); 182(100); 141(42) |

[a] ¹³C—NMR (100 MHz, CDCl₃
δ) [in ppm]; FAB-MS or EI-MS m/z (%)

Starting substances of the formula (II)

EXAMPLE (II-1)

tert-Butyl N-benzyloxycarbonyl-N-methyl-L-isoleucyl-D-lactyl-N-methyl-L-isoleucyl-D-lactyl-N-methyl-L-isoleucyl-D-lactate

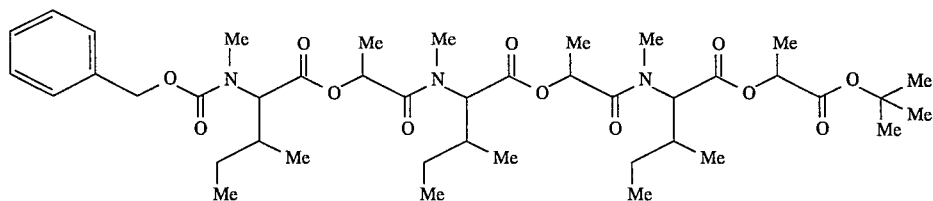

4.7 g (36.3 mmol) of N,N-diisopropylethylamine ("Hünig's base") and 4.6 g (18.1 mmol) of bis(2-oxo-3-oxazolidinyl)phosphonic chloride (BOP-Cl) are added at 0° C. to a solution of 5.8 g (16.5 mmol) of Z-L-MeIle-D-Lac-OH and 7.8 g (16.5 mmol) of H-(-L-MEIle-D-Lac-)₂-O-ᵗBu in 150 ml of methylene chloride, and the mixture is stirred for 4 hours. The reaction solution is shaken twice with water, and the organic phase is separated off, dried over sodium sulphate and then concentrated in vacuo. The crude product which remains is chromatographed over a silica gel column (silica gel 60 - Merck, particle size: 0.04 to 0.063 mm) using toluene: ethyl acetate (5:1) as the eluant. 10.3 g (77.4% of theory) of tert-butyl N-benzyloxycarbonyl-N-methyl-L-isoleucyl-D-lactyl-N-methyl-L-isoleucyl-D-lactyl-N-methyl-L-isoleucyl-D-lactate are obtained.

FAB-MS m/z (%): 805 (M⁺, 3); 749 (M⁺-H₂C=CMe₂, 10); 732 (9); 793 (10); 91 (100)

EXAMPLE (II-2)

N-Benzyloxycarbonyl-N-methyl-L-isoleucyl-D-lactyl-N-methyl-L-isoleucyl-D-lactyl-N-methyl-L-isoleucyl-D-lactic acid

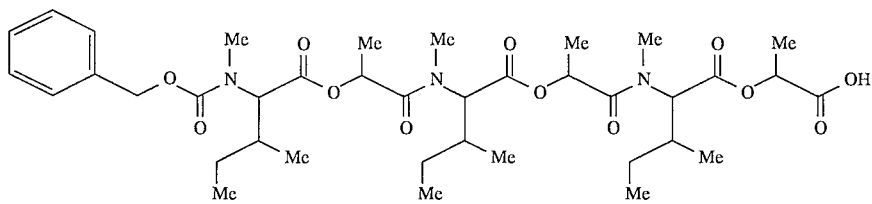

Dry hydrogen chloride gas is passed for 20 minutes into a solution, cooled to 0° C., of 9.2 g (11.2 mmol) of Z-(-L-MeIle-D-Lac-)₃-O-ᵗBu in 150 ml of absolute methylene chloride. The mixture is subsequently stirred for approximately 16 hours at room temperature and the entire reaction batch is concentrated in vacuo. 7.1 g (82.9% of theory) of N-benzyloxy-carbonyl-N-methyl-L-isoleucyl-D-lactyl-N-methyl-L- isoleucyl-D-lactyl-N-methyl-L-isoleucyl-D-lactic acid are obtained, and this can be reacted further without further purification.

MS m/z (%): 749 (M⁺, 10); 721 (1); 693 (2); 533 (0.5); 91 (100)

EXAMPLE (II-3)

Pentafluorophenyl N-benzyloxy-carbonyl-N-methyl-L-isoleucyl-D-lactyl-N-methyl-L-isoleucyl-D-lactyl-N-methyl-L-isoleucyl-D-lactate

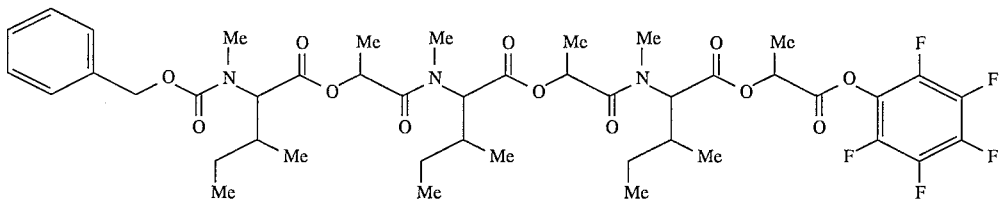

5.0 g (6.67 mmol) of Z-(L-MeIle-D-Lac-)₃-OH together with 1.23 g (6.67 mmol) of pentafluorophenol are dissolved in 125 ml of absolute ethyl acetate (inert gas atmosphere). 1.38 g (6.67 mmol) of dicyclohexylcarbodiimide (DCC) are added to this at 0° C., and stirring is continued for a further 4 hours at this temperature. After precipitated dicyclohexylurea has been filtered off, the filtrate is evaporated to dryness in vacuo, and the residue is chromatographed over a predried silica gel column (silica gel 60-Merck, particle size: 0.04 to 0.063 mm) using toluene: ethyl acetate (10:1) as the eluant.

3.3 g (54% of theory) of pentafluorophenyl N-benzyloxy-carbonyl-N-methyl-L-isoleucyl-D-lactyl-N-methyl-L-isoleucyl-D-lactate are obtained as a colourless oil.

FAB-MS m/z (%): 915 (M⁺,2); 914 (M⁺-H,4); 859 (9); 814 (I); 780 (5); 91 (100)

EXAMPLE (II-4)

N-methyl-L-isoleucyl-D-lactyl-N-methyl-L-isoleucyl-D-lactyl-N-methyl-L-isoleucyl-D-lactic acid

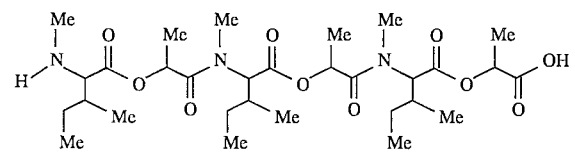

1.0 g (1.33 mmol) of Z-(-L-MeIle-D-Lac-)₃-OH are hydrogenated in 20 ml of ethanol in the presence of 0.15 g of Pd(OH)₂/charcoal [Pd content: 20] until the uptake of hydrogen has ceased (approximately 2 hours). After the catalyst has been filtered off, the entire reaction solution is concentrated in vacuo. 0.81 g (100% of theory) of N-methyl-L-isoleucyl-D-lactyl-N-methyl-L-isoleucyl-D-lactyl-N-methyl-L-isoleucyl-D-lactic acid are obtained, and this can be subjected to a cyclization reaction without further purification.

EI-MS m/z (%): 615 (M⁺,3); 600 (1); 558 (7); 472 (8); 386 (14); 100 (100)

The compounds of the general formula (II) listed in Table 2 below can be prepared analogously in the form of the LDLDLD stereoisomers.

TABLE 2

Example of compounds of the formula (II)

$$\text{A}-\text{N}(\text{Me})-\text{CH}(\text{R}^1)-\text{C}(\text{O})-\text{O}-\text{CH}(\text{R}^2)-\text{C}(\text{O})-\text{N}(\text{Me})-\text{CH}(\text{R}^3)-\text{C}(\text{O})-\text{O}-\text{CH}(\text{R}^4)-\text{C}(\text{O})-\text{N}(\text{Me})-\text{CH}(\text{R}^5)-\text{C}(\text{O})-\text{O}-\text{CH}(\text{R}^6)-\text{C}(\text{O})-\text{B} \quad \text{(II)}$$

| Ex. No. | A | $R^1$ | $R^2$ | $R^3$ | $R^4$ | $R^5$ | $R^6$ | B | Physical Data[a] |
|---|---|---|---|---|---|---|---|---|---|
| II-5 | —CO—O—CH$_2$Ph | —CH$_2$CHMe$_2$ | —Me | —CH$_2$CHMe$_2$ | —Me | —CH$_2$CHMe$_2$ | —Me | —O—C$_6$F$_5$ | 915(M$^+$, 4); 860(8); 780(3); 91(100) |
| II-6 | —CO—O—CH$_2$Ph | —CH$_2$CHMe$_2$ | —Me | —CH$_2$CHMe$_2$ | —Me | —CH$_2$CHMe$_2$ | —Me | —OH | 750(M$^+$+H); 706(2); 461(8); 91(100) |
| II-7 | —CO—OCH2Ph | —CH$_2$CHMe$_2$ | —Me | —CH$_2$CHMe$_2$ | —Me | —CH$_2$CHMe$_2$ | —Me | —O—CMe$_2$ | 805(M$^+$, 1); 749(M$^+$-H$_2$C=CMe$_2$ 12); 91(100) |
| II-8 | —CO—O—CH$_2$Ph | —CH$_2$CHMe$_2$ | —Me | —CH$_2$CHMe$_2$ | —CH$_2$Ph | —CH$_2$CHMe$_2$ | —Me | —O—C$_6$F$_5$ | 992(M$^+$+H, 1); 609(2); 514(13); 91(100) |
| II-9 | —CO—O—CH$_2$Ph | —CH$_2$CHMe$_2$ | —Me | —CH$_2$CHMe$_2$ | —CH$_2$Ph | —CH$_2$CHMe$_2$ | —Me | —OH | 826(M$^+$, 4); 769(22); 690(10); 91(100) |
| II-10 | —CO—O—CH$_2$Ph | —CH$_2$CHMe$_2$ | —Me | —CH$_2$CHMe$_2$ | —CH$_2$Ph | —CH$_2$CHMe$_2$ | —Me | —O—CMe$_2$ | 881(M$^+$, 4); 825(M$^+$–H$_2$C=CMe, 16); 807(7); 869(14); 91(100) |
| II-11 | —CH$_2$Ph | —CHMeCH$_2$Me | —CHMe$_2$ | —CHMeCH$_2$Me | —CHMe$_2$ | —CH$_2$Ph | —CHMe$_2$ | —O—C$_6$F$_5$ | 991(M$^+$+H, 6); 913(M$^+$–Ph, 3)546(2); 190(100) |
| II-12 | —CH$_2$Ph | —CHMeCH$_2$Me | —CHMe$_2$ | —CHMeCH$_2$Me | —CHMe$_2$ | —CH$_2$Ph | —CHMe$_2$ | —OH | 824(M$^+$, 3); 766(10); 704(37); 190(100) |
| II-13 | —CH$_2$Ph | —CHMeCH$_2$Me | —CHMe$_2$ | —CHMeCH$_2$Me | —CHMe$_2$ | —CH$_2$Ph | —CHMe$_2$ | —O—CMe$_2$ | 879(M$^+$, 5); 822 (10; 760(21); 704(14); 191(100) |
| II-14 | —CO—O—CH$_2$Ph | —CHMeCH$_2$Me | —CHMe$_2$ | —CHMeCH$_2$Me | —CHMe$_2$ | —CH$_2$Ph | —CHMe$_2$ | —O—C$_6$F$_5$ | 1034(M$^+$+H, 3); 589 (0.5); 489(11); 91(100) |
| II-15 | —CO—O—CH$_2$Ph | —CHMeCH$_2$Me | —CHMe$_2$ | —CHMeCH$_2$Me | —CHMe$_2$ | —CH$_2$Ph | —CHMe$_2$ | —OH | 867(M$^+$, 8)811(12); 732(10); 210(100) |
| II-16 | —CO—O—CH$_2$Ph | —CHMeCH$_2$Me | —CHMe$_2$ | —CHMeCH$_2$Me | —CHMe$_2$ | —CH$_2$Ph | —CHMe$_2$ | —O—CMe$_2$ | 923(M$^+$, 1); 868(8); 851(6); 91(100) |
| II-17 | —H | —CH$_2$CHMe$_2$ | —Me | —CHMeCH$_2$Me | —Me | —CHMeCH$_2$Me | —Me | —OH | 615(M$^+$, 5); 472(5); 386(17); 327(7); 100(100) |
| II-18 | —CH$_2$Ph | —CH$_2$CHMe$_2$ | —Me | —CHMeCH$_2$Me | —Me | —CHMeCH$_2$Me | —Me | —OH | 761(M$^+$, 1); 688(M$^+$–OCMe$_3$, 4); 642(5); 586(5); 190(100) |
| II-19 | —CH$_2$Ph | —CH$_2$CHMe$_2$ | —Me | —CHMeCH$_2$Me | —Me | —CHMeCH$_2$Me | —Me | —O—CMe$_2$ | |
| II-20 | —H | —CHMeCH$_2$Me | —CHMe$_2$ | —CHMeCH$_2$Me | —Me | —CHMeCH$_2$Me | —Me | —OH | 707(M$^+$+H, 60); 190(100) |
| II-21 | —CH$_2$Ph | —CHMeCH$_2$Me | —CHMe$_2$e | —CHMeCH$_2$Me | —Me | —CHMeCH$_2$Me | —Me | —OH | 790(M$^+$, 1); 789(M$^+$-N, 1); 717(M$^+$–OCMe$_2$, 4); 770(7); 190(100) |
| II-22 | —CH$_2$Ph | —CHMeCH$_2$Me | —CHMe$_2$ | —CHMeCH$_2$Me | —Me | —CHMeCH$_2$Me | —Me | —O—CMe$_2$ | |
| II-23 | —CH$_2$Ph | —CH—Ph | —Me | —CHMeCH$_2$Me | —Me | —CHMeCH$_2$Me | —Me | —O—CMe$_2$ | 796(M$^+$, 2); 795(M$^+$-H, 6); 723(M$^+$–OCMe$_2$, 3); 704(47); 224(100) |
| II-24 | —H | —CH—Ph | —Me | —CHMeCH$_2$Me | —Me | —CHMeCH$_2$Me | —Me | —O—CMe$_2$ | 705(M$^+$, 2), 632(M$^+$–OCMe$_2$, 7), 614(26); 558(39); 269(100) |

[a]FAB-MS or EI-MS m/z (%)

Examples of the preparation of the cyclic depsipeptides having 24 ring atoms:
1. Preparation of the compounds of the formula (Ia).

BOP-Cl (0.124 mmol) was added at 0° C. to a solution of the compound of the formula IIc (0.104 mmol) and Hünig's base (0.258 mmol) in dichloromethane (100 ml), and stirring of the mixture was continued for 24 hours at room temperature. After this time had elapsed, the same amount of BOP-Cl and base were added, and the mixture was stirred for a further 24 hours. The solution was washed twice using saturated sodium hydrogen carbonate solution, dried over sodium sulphate and concentrated. The residue was purified by column chromatography using cyclohexane/ethyl acetate 2:1 as the eluant.

Compounds of the formula (Ia) were obtained in which the substituents have the following meaning (Table 3):

Preparation of the compounds of the formula (IIIa)

HCl gas was passed for 1.5 hours at 0° C. into a solution of the tert-butyl ester of the formula (IVa) (1.609 mmol) in dichloromethane (40 ml). The mixture was subsequently heated to room temperature, and stirring was continued for 12 hours. The solution was evaporated on a rotary evaporator and the residue dried under high vacuum. The residue was reacted without further purification.

Compounds of the formula (IIIa) in which the substituents have the meaning given below were obtained analogously (Table 5):

TABLE 3

| No. | $R^{1a}$ | $R^{2a}$ | $R^{3a}$ | $R^{4a}$ | $R^{5a}$ | $R^{6a}$ | $R^{7a}$ | $R^{8a}$ | $R^{9a}$ | $R^{10a}$ | $R^{11a}$ | $R^{12a}$ | FAB-MS m/z (%) |
|---|---|---|---|---|---|---|---|---|---|---|---|---|---|
| 1a | Et | Et | Me | s-Bu | Bn | s-Bu | Me | s-Bu | Bn | s-Bu | Et | Et | |
| 2a | Propyl | Propyl | " | " | " | " | " | " | " | " | Propyl | Propyl | |
| 3a | i-Propyl | i-Propyl | " | " | " | " | " | " | " | " | i-Propyl | i-Propyl | |
| 4a | Me | Me | " | s-Bu | " | s-Bu | " | s-Bu | " | s-Bu | Me | Me | 948(82, (+H)$^+$) |
| 5a | Me | Me | " | i-Pr | " | i-Pr | " | i-Pr | " | i-Pr | Me | Me | 915(100, (M+Na)$^+$) 893(55, (M+H)$^+$) |
| 6a | Me | Me | " | Bn | " | Bn | " | Bn | " | Bn | Me | Me | 1107(100, (M+Na)$^+$) 1085(8, (M+H)$^+$) |
| 7a | Me | Me | " | s-Bu | 2-Cl—Bn | s-Bu | " | s-Bu | 2-Cl—Bn | s-Bu | Me | Me | |
| 8a | Me | Me | " | " | 2-Cl—Bn | " | " | " | 3-Cl—Bn | " | Me | Me | |
| 9a | Me | Me | " | " | 4-Cl—Bn | " | " | " | 4-Cl—Bn | " | Me | Me | |
| 10a | Propyl | i-Propyl | " | " | —Bn | " | " | " | —Bn | " | Propyl | i-Propyl | |

Me = methyl
Bu = butyl
Pr = propyl
Et = ethyl
Bn = benzyl

Examples of the preparation of the compounds of the formula (IIc)

A solution of an open-chain octadepsipeptide of the formula (IIIa) (1.222 mmol) in ethanol (50 ml) was hydrogenated in the presence of Pd(OH)$_2$/C (20%: 200 mg) until the uptake of hydrogen had ceased (approximately 2 hours). After the catalyst had been filtered off, pure compound of the formula IIc was obtained, and this was reacted further without additional purification.

In accordance with this protocol, compounds of the formula (IIc) were obtained in which the substituents have the meaning shown in Table 4.

TABLE 4

| No. | $R^{1a}$ | $R^{2a}$ | $R^{3a}$ | $R^{4a}$ | $R^{5a}$ | $R^{6a}$ | $R^{7a}$ | $R^{8a}$ | $R^{9a}$ | $R^{10a}$ | $R^{11a}$ | $R^{12a}$ |
|---|---|---|---|---|---|---|---|---|---|---|---|---|
| 11 | Et | Et | Me | s-Bu | Bn | s-Bu | Me | s-Bu | Bn | s-Bu | Et | Et |
| 12 | Propyl | Propyl | " | " | " | " | " | " | " | " | Propyl | Propyl |
| 13 | i-Propyl | i-Propyl | " | " | " | " | " | " | " | " | i-Propyl | i-Propyl |
| 14 | Me | Me | " | " | " | " | " | " | " | " | Me | Me |
| 15 | Me | Me | " | i-Pr | " | i-Pr | " | i-Pr | " | i-Pr | Me | Me |
| 16 | M4 | Me | " | Bn | " | Bn | " | Bn | " | Bu | Me | Me |
| 17 | Me | Me | " | s-Bu | 2-Cl—Bn | s-Bu | " | s-Bu | 2-Cl—Bn | s-Bu | Me | Me |
| 18 | Me | Me | " | " | 3-Cl—Bn | " | " | " | 3-Cl—Bn | " | Me | Me |
| 19 | Me | Me | " | " | 4-Cl—Bn | " | " | " | 4-Cl—Bn | " | Me | Me |
| 20 | Propyl | i-Propyl | " | " | —Bn | " | " | " | —Bn | " | Propyl | i-Propyl |

Me = methyl
Et = ethyl
s-Bu = s-butyl
Bn = benzyl

TABLE 5

| No. | $R^{1a}$ | $R^{2a}$ | $R^{3a}$ | $R^{4a}$ | $R^{5a}$ | $R^{6a}$ | $R^{7a}$ | $R^{8a}$ | $R^{9a}$ | $R^{10a}$ | $R^{11a}$ | $R^{12a}$ | A |
|---|---|---|---|---|---|---|---|---|---|---|---|---|---|
| 21 | Et | Et | Me | s-Bu | Bn | s-Bu | Me | s-Bu | Bn | s-Bu | Et | Et | Bn |
| 22 | Propyl | Propyl | " | " | " | " | " | " | " | " | Propyl | Propyl | " |
| 23 | i-Propyl | i-Propyl | " | " | " | " | " | " | " | " | i-Propyl | i-Propyl | " |
| 24 | Me | Me | " | " | " | " | " | " | " | " | Me | Me | " |
| 25 | Me | Me | " | i-Pr | " | i-Pr | " | i-Pr | " | i-Pr | Me | Me | " |
| 26 | M4 | Me | " | Bn | " | Bn | " | Bn | " | Bn | Me | Me | " |
| 27 | Me | Me | " | s-Bu | 2-Cl—Bn | s-Bu | " | s-Bu | 2-Cl—Bn | s-Bu | Me | Me | " |
| 28 | Me | Me | " | " | 2-Cl—Bn | " | " | " | 3-Cl—Bn | " | Me | Me | " |
| 29 | Me | Me | " | " | 4-Cl—Bn | " | " | " | 4-Cl—Bn | " | Me | Me | " |
| 30 | Propyl | i-Propyl | " | " | —Bn | " | " | " | —Bn | " | Propyl | i-Propyl | " |

Me = methyl
Et = ethyl
s-Bu = s-butyl
Bn = benzyl

Preparation of the compounds of the formula (IVa)

A solution of ethyldiisopropylamine (0.912 mmol) and BOP-Cl (0.438 mmol) was added at 0° C. to a solution of the tetradepsipeptides of the formula (VIa) and (Va), in each case (2.52 mmol), in dichloromethane (15 ml). Stirring was continued for 1 hour at 0° C. and for 1.5 hours at room temperature, and the mixture was diluted with 20 ml of dichloromethane, washed twice with a little water, dried over $Na_2SO_4$ and concentrated. The residue was purified on silica gel using cyclohexane-t-BuOMe=2:1 as the eluant.

Preparation of the compounds of the formula (Va)

HCl gas was passed for 2 hours at 0° C. into a solution of the tetradepsipeptide of the formula (VIIa), (2.848 mmol) in dichloromethane (50 ml).

Stirring was subsequently continued for 8 hours at room temperature, and the mixture was concentrated and dried under a high vacuum. The residue was reacted without further purification.

Preparation of the compounds of the formula (VIa)

A solution of the tetradepsipeptide of the formula (VIIa) (9.53 mmol) in ethanol (37 ml) was treated with $Pd(OH)_2/C$ (20%) (0.6 g), and the mixture was hydrogenated for approximately 3 hours at room temperature and under atmospheric pressure. The reaction mixture was filtered and concentrated, and the residue was separated on silica gel using t-BuOMe/cyclohexane/ethanol=1:1:0.5 as the eluant.

Preparation of the compounds of the formula (VIIa)

A solution, cooled to 0° C., of the dipepsipeptide IXa (22.9 mmol) and of the didepsipeptide VIIIa (27.5 mmol) in dichloromethane (80 ml) was treated with diisopropylethylamine (57.3 mmol) and BOP-Cl (29.8 mmol), and the mixture was stirred for 1 hour at 0° C. and for 1 hour at room temperature. After the precipitate had been filtered off, the solution was diluted with dichloromethane, washed three times with a little water, dried over sodium sulphate and concentrated. The residue was separated on silica gel using cyclohexane/ethyl acetate=15:1 as the eluant.

We claim:

1. A composition comprising approximately equal amounts by weight of a compound selected from the group consisting of praziquantel and epsiprantel; and one compound is selected from the group consisting of cyclo(-MeLeu-D-Lac-MeLeu-D-PhLac-MeLeu-D-Lac-MeLeu-D-PhLac-) and cyclo(-MeLeu-D-Lac-MeLeu-D-p-MorPhLac-MeLeu-D-Lac-MeLeu-D-p-MorPhLac-).

2. A composition according to claim 1, comprising approximately equal parts by weight of (A) praziquantel, and (B) cyclo(-MeLeu-D-Lac-MeLeu-D-PhLac-MeLeu-D-Lac-MeLeu-D-PhLac-).

3. A composition according to claim 1, comprising approximately equal parts by weight of (A) praziquantel, and (B) cyclo(-MeLeu-D-Lac-MeLeu-D-p-MorPhLac-MeLeu-D-Lac-MeLeu-D-p-MorPhLac-).

4. A composition according to claim 1, comprising approximately equal parts by weight of (A) epsiprantel, and (B) cyclo(-MeLeu-D-Lac-MeLeu-D-p-MorPhLac-MeLeu-D-Lac-MeLeu-D-p-MorPhLac-).

5. A composition according to claim 1, comprising approximately equal parts by weight of (A) epsiprantel, and (B) cyclo(-MeLeu-D-Lac-MeLeu-D-p-MorPhLac-MeLeu-D-Lac-MeLeu-D-p-MorPhLac-) epsiprantel.

* * * * *